(12) United States Patent
Janssens et al.

(10) Patent No.: US 7,148,214 B1
(45) Date of Patent: Dec. 12, 2006

(54) ANTIHISTAMINIC SPIRO COMPOUNDS

(75) Inventors: Frans Eduard Janssens, Bonheiden (BE); Joseph Elisabeth Leenaerts, Rijkevorsel (BE)

(73) Assignee: Janssen Pharmaceutica, N.V., Beerse (BE)

( * ) Notice: Subject to any disclaimer, the term of this patent is extended or adjusted under 35 U.S.C. 154(b) by 0 days.

(21) Appl. No.: 09/868,535

(22) PCT Filed: Dec. 15, 1999

(86) PCT No.: PCT/EP99/10176

§ 371 (c)(1),
(2), (4) Date: Jul. 26, 2001

(87) PCT Pub. No.: WO00/37470

PCT Pub. Date: Jun. 29, 2000

(30) Foreign Application Priority Data

Dec. 19, 1998 (EP) .............................. 98204347

(51) Int. Cl.
*A61K 31/55* (2006.01)
*A61K 31/44* (2006.01)
*A61P 37/08* (2006.01)
*C07D 225/04* (2006.01)
*C07D 401/00* (2006.01)

(52) U.S. Cl. .............................. 514/211.1; 514/211.12; 514/212.02; 514/278; 540/466; 540/543; 546/18

(58) Field of Classification Search .............. 514/211.1, 514/211.12, 212.02, 278; 540/543, 466; 546/18
See application file for complete search history.

(56) References Cited

FOREIGN PATENT DOCUMENTS

| EP | 0 127 412 B1 | 10/1990 |
|----|--------------|---------|
| EP | 0 393 738 A | 10/1990 |
| EP | 0 518 434 A | 12/1992 |
| WO | 97 24356 A | 7/1997 |

*Primary Examiner*—Brenda Coleman
(74) *Attorney, Agent, or Firm*—Woodcock Washburn LLP

(57) ABSTRACT

This invention concerns the compounds of formula

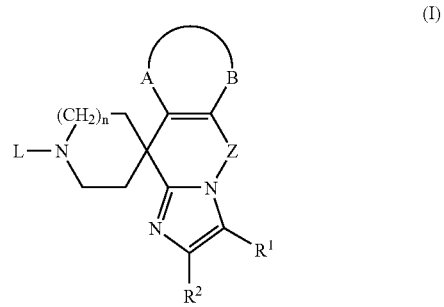

(I)

or a prodrug, a N-oxide, an addition salt, a quaternary amine or a stereochemically isomeric form thereof wherein $R^1$, $R^2$, —A—B—, L, and n have the meaning given in the description. The invention relates to preparations and compositions of the present compounds and their use as medicines.

15 Claims, No Drawings

ANTIHISTAMINIC SPIRO COMPOUNDS

CROSS REFERENCE TO RELATED APPLICATIONS

This application is a national stage entry under 35 U.S.C. §371 of PCT/EP99/10176, filed Dec. 15, 1999.

The present invention is concerned with spiro compounds having antihistarminic activity. It further relates to their use as a medicine, their preparation as well as compositions comprising them.

WO 97/24356, published on Jul. 10, 1997, discloses 4-(imidazo-azepine) piperidine spiro derivatives as intermediates in the preparation of 1-(1,2-disubstituted piperidinyl)-4-(imidazo-azepine) piperidine spiro derivatives having tachykinin antagonistic activity.

Surprisingly, the 4-(imidazo-azepine) piperidine spiro derivatives of the present invention show an interesting antihistarminic activity profile.

The present invention concerns compounds of formula (I) for use as a medicine, characterized in that the compounds of formula (I) are defined as

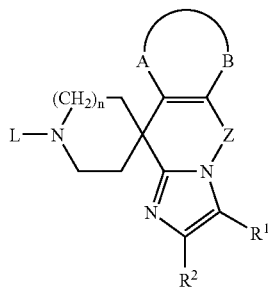

(I)

their prodrugs, N-oxides, addition salts, quaternary amines and stereochemically isomeric forms wherein $R^1$ is hydrogen, $C_{1-6}$alkyl, halo, formyl, carboxyl, $C_{1-6}$alkyloxycarbonyl, $C_{1-6}$alkylcarbonyl, $N(R^3R^4)C(=O)$—, $N(R^3R^4)C(=O)N(R^5)$—, ethenyl substituted with carboxyl or $C_{1-6}$alkyloxycarbonyl, or $C_{1-6}$alkyl substituted with hydroxy, carboxyl, $C_{1-6}$alkyloxy, $C_{1-6}$alkyloxycarbonyl, $N(R^3R^4)C(=O)$—, $C_{1-6}$alkylC(=O)N(R^5)—, $C_{1-6}$alkylS(=O)_2N(R^5)$— or $N(R^3R^4)C(=O)N(R^5)$—;

wherein each $R^3$ and each $R^4$ independently are hydrogen or $C_{1-4}$alkyl;

$R^5$ is hydrogen or hydroxy;

$R^2$ is hydrogen, $C_{1-6}$alkyl, hydroxy$C_{1-6}$alkyl, $C_{1-6}$alkyloxy$C_{1-6}$alkyl, $N(R^3R^4)C(=O)$—, aryl or halo;

n is 1 or 2;

—A—B— represents a bivalent radical of formula

—Y—CH=CH— (a-1);
—CH=CH—Y— (a-2); or
—CH=CH—CH=CH— (a-3);

wherein each hydrogen atom in the radicals (a-1) to (a-3) may independently be replaced by $R^6$ wherein $R^6$ is selected from $C_{1-6}$alkyl, halo, hydroxy, $C_{1-6}$alkyloxy, ethenyl substituted with carboxyl or $C_{1-6}$alkyloxycarbonyl, hydroxy$C_{1-6}$alkyl, formyl, carboxyl and hydroxycarbonyl$C_{1-6}$alkyl; each Y independently is a bivalent radical of formula —O—, —S— or —NR$^7$—; wherein $R^7$ is hydrogen, $C_{1-6}$alkyl or $C_{1-6}$alkylcarbonyl;

Z is a bivalent radical of formula

| —(CH$_2$)$_p$— | (b-1), | —CH$_2$—O— | (b-4), |
| —CH=CH— | (b-2), | —CH$_2$—C(=O)— | (b-5), or |
| —CH$_2$—CHOH— | (b-3), | —CH$_2$—C(=NOH)— | (b-6), | provided that the bivalent radicals (b-3), (b-4), (b-5) and (b-6) are connected to the nitrogen of the imidazole ring via their —CH$_2$— moiety;

wherein p is 1, 2, 3 or 4;

L is hydrogen; $C_{1-6}$alkyl; $C_{2-6}$alkenyl; $C_{1-6}$alkylcarbonyl; $C_{1-6}$alkyloxycarbonyl;

$C_{1-6}$alkyl substituted with one or more substituents each independently selected from hydroxy, carboxyl, $C_{1-6}$alkyloxy, $C_{1-6}$alkyloxycarbonyl, aryl, aryloxy, cyano or $R^8$HN— wherein $R^8$ is hydrogen, $C_{1-6}$alkyl, $C_{1-6}$alkyloxycarbonyl, $C_{1-6}$alkylcarbonyl; or

| L represents a radical of formula | |
| -Alk-Y$^1$-Het$^1$ | (c-1), |
| -Alk-NH—CO-Het$^2$ | (c-2) or |
| -Alk-Het$^3$ | (c-3); wherein |
| Alk represents $C_{1-4}$ alkanediyl; | |
| Y$^1$ represents O, S or NH; | |

Het$^1$, Het$^2$ and Het$^3$ each represent furanyl, tetrahydrofuranyl, thienyl, oxazolyl, thiazolyl or imidazolyl each optionally substituted with one or two $C_{1-4}$alkyl substituents; pyrrolyl or pyrazolyl optionally substituted with formyl, hydroxy$C_{1-4}$alkyl, hydroxycarbonyl, $C_{1-4}$alkyloxycarbonyl or with one or two $C_{1-4}$alkyl substituents; thiadiazolyl or oxadiazolyl optionally substituted with amino or $C_{1-4}$alkyl; pyridinyl, pyrimidinyl, pyrazinyl or pyridazinyl each optionally substituted with $C_{1-4}$alkyl, $C_{1-4}$alkyloxy, amino, hydroxy or halo; and Het$^3$ may also represent 4,5-dihydro-5-oxo-1H-tetrazolyl substituted with $C_{1-4}$alkyl, 2-oxo-3-oxazolidinyl, 2,3-dihydro-2-oxo-1H-benzimidazol-1-yl or a radical of formula

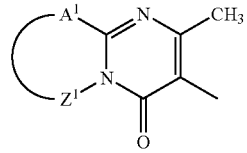

wherein $A^1$—$Z^1$ represents S—CH=CH, S—CH$_2$—CH$_2$, S—CH$_2$—CH$_2$—CH$_2$, CH=CH—CH=CH, or CH$_2$—CH$_2$—CH$_2$—CH$_2$;

aryl is phenyl or phenyl substituted with 1, 2 or 3 substituents each independently selected from halo, hydroxy, $C_{1-4}$alkyl, polyhalo$C_{1-4}$alkyl, cyano, aminocarbonyl, $C_{1-4}$alkyloxy or polyhalo$C_{1-4}$alkyloxy.

The compounds of formula (I) are deemed novel provided that 5,6-dihydrospiro[imidazo[2,1-b][3]benzazepine-11[11H],4'-piperidine] and pharmaceutically acceptable addition salts thereof are not included and thus the present invention also relates to the compounds of formula (I) as defined hereinabove provided that 5,6-dihydrospiro[imidazo[2,1-b][3]benzazepine-11[11H],4'-piperidine] and pharmaceutically acceptable addition salts thereof are not included.

The term prodrug as used throughout this text means the pharmacologically acceptable derivatives, e.g. esters and amides, such that the resulting biotransformation product of the derivative is the active drug as defined in the compounds of formula (I). The reference by Goodman and Gilman (The Pharmacological Basis of Therapeutics, $8^{th}$ ed., McGraw-Hill, Int. Ed. 1992, "Biotransformation of Drugs", p. 13–15) describing prodrugs generally, is hereby incorporated.

As used herein $C_{1-4}$alkyl as a group or part of a group defines straight or branched chain saturated hydrocarbon radicals having from 1 to 4 carbon atoms such as methyl, ethyl, propyl, 1-methylethyl, butyl and the like; $C_{1-6}$alkyl as a group or part of a group defines straight or branched chain saturated hydrocarbon radicals having from 1 to 6 carbon atoms such as the groups defined for $C_{1-4}$alkyl and pentyl, hexyl, 2-methylpropyl, 2-methylbutyl and the like; $C_{2-6}$alkenyl as a group or part of a group defines straight and branched chain hydrocarbon radicals containing one double bond and having from 2 to 6 carbon atoms such as ethenyl, 2-propenyl, 2-butenyl, 2-pentenyl, 3-pentenyl, 3-methyl-2-butenyl, 3-hexenyl and the like.

As used herein before, the term (=O) forms a carbonyl moiety when attached to a carbon atom and a sulfonyl moiety when attached twice to a sulfur atom. The term (=NOH) forms a hydroxylimine moiety when attached to a carbon atom.

The term halo is generic to fluoro, chloro, bromo and iodo. As used in the foregoing and hereinafter, polyhalo$C_{1-4}$alkyl as a group or part of a group is defined as mono- or polyhalosubstituted $C_{1-4}$alkyl, in particular methyl with one or more fluoro atoms, for example, difluoromethyl or trifluoromethyl. In case more than one halogen atoms are attached to an alkyl group within the definition of polyhalo$C_{1-4}$alkyl, they may be the same or different.

When any variable (e.g. $R^3$, $R^4$ etc.) occurs more than one time in any constituent, each definition is independent.

It will be appreciated that some of the compounds of formula (I), their prodrugs, N-oxides, addition salts, quaternary amines and stereochemically isomeric forms may contain one or more centers of chirality and exist as stereochemically isomeric forms.

The term "stereochemically isomeric forms" as used hereinbefore defines all the possible stereoisomeric forms which the compounds of formula (I), their prodrugs, N-oxides, addition salts, quaternary amines or physiologically functional derivatives may possess. Unless otherwise mentioned or indicated, the chemical designation of compounds denotes the mixture of all possible stereochemically isomeric forms, said mixtures containing all diastereomers and enantiomers of the basic molecular structure as well as each of the individual isomeric forms of formula (I), their prodrugs, N-oxides, addition salts or quaternary amines substantially free, i.e. associated with less than 10%, preferably less than 5%, in particular less than 2% and most preferably less than 1% of the other isomers. Stereochemically isomeric forms of the compounds of formula (I) are obviously intended to be embraced within the scope of this invention.

For therapeutic use, the addition salts of the compounds of formula (I) are those wherein the counterion is pharmaceutically acceptable. However, salts of acids and bases which are not-pharmaceutically acceptable may also find use, for example, in the preparation or purification of a pharmaceutically acceptable compound. All salts, whether pharmaceutically acceptable or not are included within the ambit of the present invention.

The pharmaceutically acceptable acid and base addition salts as mentioned hereinabove are meant to comprise the therapeutically active non-toxic acid and base addition salt forms which the compounds of formula (I) are able to form. The pharmaceutically acceptable acid addition salts can conveniently be obtained by treating the base form with such appropriate acid. Appropriate acids comprise, for example, inorganic acids such as hydrohalic acids, e.g. hydrochloric or hydrobromic acid, sulfuric, nitric, phosphoric and the like acids; or organic acids such as, for example, acetic, propanoic, hydroxyacetic, lactic, pyruvic, oxalic (i.e. ethanedioic), malonic, succinic (i.e. butanedioic acid), maleic, fumaric, malic, tartaric, citric, methanesulfonic, ethanesulfofiic, benzenesulfonic, p-toluenesulfonic, cyclamic, salicylic, p-aminosalicylic, pamoic and the like acids.

Conversely said salt forms can be converted by treatment with an appropriate base into the free base form.

The compounds of formula (I) containing an acidic proton may also be converted into their non-toxic metal or amine addition salt forms by treatment with appropriate organic and inorganic bases. Appropriate base salt forms comprise, for example, the ammonium salts, the alkali and earth alkaline metal salts, e.g. the lithium, sodium, potassium, magnesium, calcium salts and the like, salts with organic bases, e.g. the benzathine, N-methyl-D-glucamine, hydrabamine salts, and salts with amino acids such as, for example, arginine, lysine and the like.

The term addition salt as used hereinabove also comprises the solvates which the compounds of formula (I) as well as the salts thereof, are able to form. Such solvates are for example hydrates, alcoholates and the like.

Some of the compounds of formula (a) may also exist in their tautomeric form. Such forms although not. explicitly indicated in the above formula are intended to be included within the scope of the present invention.

An interesting group of compounds consists of those compounds of formula (I) wherein L is hydrogen, $C_{1-6}$alkyl, $C_{1-6}$alkylcarbonyl, $C_{1-6}$alkyloxycarbonyl or $C_{1-6}$alkyl substituted with hydroxy, carboxyl, $C_{1-6}$alkyloxy or $C_{1-6}$alkyloxycarbonyl;

Another interesting group of compounds consists of those compounds of formula (I) wherein —A—B— is a bivalent radical of formula —CH=CH—CH=CH— (a-3).

Also interesting compounds are those compounds of formula (I) wherein —A—B— is a bivalent radical of formula —CH=CH—Y— (a-2).

Further interesting compounds are those compounds of formula (I) wherein Z is —(CH$_2$)$_p$— (b-1), —CH=CH— (b-2), or —CH$_2$—O— (b-4).

Other interesting compounds are those compounds of formula (I) wherein L is hydrogen, $C_{1-6}$alkyl, carboxy$C_{1-6}$alkyl, $C_{1-6}$alkyloxycarbonyl, or $C_{1-6}$alkyloxycarbonyl$C_{1-6}$alkyl.

Again other interesting compounds are those compounds of formula (I) wherein L is hydroxy$C_{1-6}$alkyl or $C_{1-6}$alkyl substituted with aryl and $C_{1-6}$alkyloxycarbonyl.

Also further interesting compounds are those compounds of formula (I) wherein $R^1$ is hydroxy$C_{1-6}$alkyl, formyl, $C_{1-6}$alkyloxycarbonyl, N($R^3R^4$)C(=O)—, halo or hydrogen.

Other interesting compounds are those compounds of formula (I) wherein $R^1$ is $C_{1-6}$alkyloxy$C_{1-6}$alkyl.

Special compounds are those compounds of formula (I) wherein one or more of the following restrictions apply:

—A—B— is a bivalent radical of formula —CH=CH—CH=CH— (a-3) wherein each hydrogen may independently be replaced by $C_{1-6}$alkyl, $C_{1-6}$alkyloxy, halo or hydroxy;

Z is —$(CH_2)_p$— wherein p is 1,2,3 or 4, —$CH_2$—C(=O)—, —$CH_2$—CHOH—, —CH=CH—, —$CH_2$—O—;

L is hydrogen, $C_{1-6}$alkyl or $C_{1-6}$alkyloxycarbonyl;

$R^1$ is hydrogen, formyl, carboxyl, amide, halo, $C_{1-6}$alkyloxycarbonyl, $C_{1-6}$alkyl substituted with hydroxy, $C_{1-6}$alkyloxy, —NH—C(=O)—$C_{1-6}$alkyl, —NH—C(=O)—$NH_2$, —NH—$SO_2$—$C_{1-6}$alkyl;

$R^2$ is hydroxy$C_{1-6}$alkyl, $C_{1-6}$alkyloxy$C_{1-6}$alkyl, halo, amide.

The most preferred compounds are:

5,6-dihydrospiro[11H-imidazo[2,1-b][3]benzazepine-11, 4'-piperidine]-3-carboxamide dihydrochloride (comp. 17);

1'-butyl-5,6-dihydrospiro[imidazo[2,1-b][3]benzazepine-11-[11H],4'-piperidine] (comp. 3);

6,11-dihydro-1'-methylspiro[5H-imidazo[2,1-b][3]benzazepine-11,4'-piperidine]cyclohexylsulfamate (1:2) (comp. 1);

6,11-dihydrospiro[5-imidazo[2,1-b][3]benzazepine-11,4'-piperidine]-3-methanol] (E)-2-butenedioate (2:1) (comp. 18a);

3-chloro-6,11-dihydrospiro[5H-imidazo[2,1-b][3]benzazepine-11,4'-piperidine] (E)-2-butenedioate (1:1) (comp. 20);

6,11-dihydro-3-(methoxymethyl)spiro[5H-imidazo[2,1-b][3]benzazepine-11,4'-piperidine]. (E)-2-butenedioate (1:1) (comp. 58);

6,11-dihydro-1'-(2-hydroxyethyl)spiro[5H-imidazo[2,1-b][3]benzazepine-11,4'-piperidine]-3-carboxamide (comp. 62);

6,11-dihydro-1'-methylspiro[5H-imidazo[2,1-b][3]benzazepine-11,4'-piperidine]-3-carboxamide monohydrate (comp. 80);

ethyl 3-(aminocarbonyl)-6,11-dihydro-α-phenylspiro[5H-imidazo[2,1-b][3]-benzazepine-11,4'-piperidine]-1'-propanoate monohydrochloride (comp. 64);

3-(aminocarbonyl)-6,11-dihydrospiro[5H-imidazo[2,1-b][3]-benzazepine-11,4'-piperidine]-1'-carboxylate (comp. 79);

spiro[10H-imidazo[1,2-a]thieno[3,2-d]azepine-10,4'-piperidine] (comp. 56a);

6,11-dihydrospiro[5H-imidazo[2,1-b][3]benzazepine-11, 4'-piperidine]-2,3-dicarboxamide dihydrochloride monohydrate (comp. 53);

a prodrug, a N-oxide, an addition salt, a quaternary amine or a stereochemically isomeric form thereof.

The present invention also concerns novel compounds of formula

TABLE 9

| Sample | Coating (%/% heptdmac/silane) | 1 day unwashed | 30 days unwashed | 1 day wash | 30 days wash | 87 days wash |
|---|---|---|---|---|---|---|
| 97-100-36A (2 min dwell) | 2.0/4.0 | <150, <125 | <50 | <25, <25 | <5 | <1, <1 |
| 97-100-36B (2 min) | 4.0/8.0 | <25, <25 | <25 | <25, <25 | <5 | <1, <1 |
| 97-100-36C (2 min) | 4.0/4.0 | <175, <150 | <150 | <50, <25 | <5 | <1, <1 |
| 97-100-36C (2 min) | Diluted, 4.0/4.0 | <50, <100 | <150 | <25, <25 | <5 | 0, <1 | their N-oxides, addition salts, quaternary amines and stereochemically isomeric forms, wherein $R^1$ is hydrogen, $C_{1-6}$alkyl, halo, formyl, carboxyl, $C_{1-6}$alkyloxycarbonyl, $C_{1-6}$alkylcarbonyl, $N(R^3R^4)C(=O)$—, $N(R^3R^4)C(=O)N(R^5)$—, ethenyl substituted with carboxyl or $C_{1-6}$alkyloxycarbonyl, or $C_{1-6}$alkyl substituted with hydroxy, carboxyl, amino, $C_{1-6}$alkyloxy, $C_{1-6}$alkyloxycarbonyl, $N(R^3R^4)C(=O)$—, $C_{1-6}$alkylC(=O)N($R^5$)—, $C_{1-6}$alkylS(=O)$_2$N($R^5$)— or $N(R^3R^4)C(=O)N(R^5)$—;

wherein each $R^3$ and each $R^4$ independently are hydrogen or $C_{1-4}$alkyl;

$R^5$ is hydrogen or hydroxy;

—A—B—, Z, $R^2$, and n are as defined for compounds of formula (I); and

P represents a protective group for example, benzyl, or those protective groups mentioned in Chapter 7 of "Protective Groups in Organic Synthesis" by T. Greene and P. Wuyts (John Wiley & Sons, Inc. 1991), provided that 6,11-dihydro-1'-(phenylmethyl)-5H-spiro[imidazo[2,1-b][3]benzazepine-11,4'-piperidine] (E)-2-butenedioate (1:2) is not included.

The compounds of formula (II-a) are useful for the preparation of the compounds of formula (I).

Interesting compounds are those compounds of formula (II-a) wherein P is benzyl.

Also interesting compounds are those compounds of formula (II-a) wherein $R^1$ is hydrogen, halo, formyl, $N(R^3R^4)C(=O)$—, or $C_{1-6}$alkyl substituted with hydroxy, amino, $C_{1-6}$alkylC(=O)N($R^5$)—, $C_{1-6}$alkylS(=O)$_2$N($R^5$)— or $N(R^3R^4)C(=O)N(R^5)$—.

Further interesting compounds are those compounds of formula (II-a) wherein —A—B— is a bivalent radical of formula (a-3) wherein each hydrogen atom may independently be replaced by $C_{1-6}$alkyl, halo, hydroxy, or $C_{1-6}$alkyloxy.

Again further interesting compounds are those compounds of formula (II-a) wherein Z is a bivalent radical of formula (b-1) and n is 1.

Compounds of formula (I), can be prepared by deprotecting an intermediate of formula (II), wherein P is a protecting group, for example, benzyl, or those protective groups mentioned in Chapter 7 of "Protective Groups in Organic Synthesis" by T. Greene and P. Wuyts (John Wiley & Sons, Inc. 1991). Said deprotection reaction can be performed by, for example, catalytic hydrogenation in the presence of hydrogen and an appropriate catalyst in a reaction inert solvent. A suitable catalyst in the above reaction is, for example, platinum-on-charcoal, palladium-on-charcoal, and the like. An appropriate reaction-inert solvent for said reaction is, for example, an alcohol, e.g. methanol, ethanol, 2-propanol and the like, an ester, e.g. ethylacetate and the like, an acid, e.g. acetic acid and the like. The thus obtained deprotected compounds can optionally further be derivatized either by replacing the hydrogen on the piperidine nitrogen by a moiety belonging to L, or by introducing on the imidazole moiety a $R^1$ group or a $R^2$ group or a $R^1$ and $R^2$ group, or by derivatizing both the piperidine moiety and the imidazole moiety.

An intermediate of formula II can also first be derivatized at the imidazole moiety by introducing a $R^1$ group or a $R^2$ group or a $R^1$ and $R^2$ group, resulting in an intermediate of formula (II-a), and then be deprotected, followed optionally by a derivation at the piperidine nitrogen.

TABLE 15

| Sample | Coating (%/% heptdmac/silane) | Dip | Activity, mU/cm² | | | | | |
|---|---|---|---|---|---|---|---|---|
| | | | 1 day unwashed | 11 days unwashed | 1 day washed | 11 days wash | 25 days wash | 43 days wash |
| 97-100-92A | 0.5/0.5 | Double | <25 | <25, <25 | <2 | <1, <1 | <1, <1, <5, <2, <2, <2 | — |
| 97-100-92B | 0.5/0.5 | Dip/wash/Dip | <25 | <10, <25 | <2 | <1, <1 | <2, <2, <2, <2, <1, <2 | — |
| 97-100-92D | 0.5/2.0 | Double | <10 | | <5 | — | <5, <2 | <1, <2 |
| 97-100-92E | 0.5/2.0 | Dip/wash/Dip | <25 | | <2 | — | <2, <2 | <1, <1 |

Alternatively, compounds of formula (I), wherein Z is a bivalent radical of formula —$CH_2$—C(=O)— (b-5), said compounds being represented by formula (I-a), can be prepared by cyclizing an intermediate of formula (III) in the presence of an acid, e.g. trifluoromethanesulfonic acid and the like.

TABLE 16

| Sample | Coating (%/% heptdmac/silane) | Dip | Activity, mU/cm² | |
|---|---|---|---|---|
| | | | 1 day unwashed | 1 day |
| 97-100-92C | 0.5/0.5 | Dip/wash/Dip | <125 | <50 |
| 97-100-92F | 0.5/2.0 | Dip/wash/Dip | <50 | <10 |

The compounds of formula (I) may further be prepared by converting compounds of formula (I) into each other according to art-known group transformation reactions.

The compounds of formula (I) may be converted to the corresponding N-oxide forms following art-known procedures for converting a trivalent nitrogen into its N-oxide form. Said N-oxidation reaction may generally be carried out by reacting the starting material of formula (I) with an appropriate organic or inorganic peroxide. Appropriate inorganic peroxides comprise, for example, hydrogen peroxide, alkali metal or earth alkaline metal peroxides, e.g. sodium peroxide, potassium peroxide; appropriate organic peroxides may comprise peroxy acids such as, for example, benzenecarboperoxoic acid or halo substituted benzenecarboperoxoic acid, e.g. 3-chlorobenzenecarboperoxoic acid, peroxoalkanoic acids, e.g. peroxoacetic acid, alkylhydroperoxides, e.g. t.butyl hydro-peroxide. Suitable solvents are, for example, water, lower alcohols, e.g. ethanol and the like, hydrocarbons, e.g. toluene, ketones, e.g. 2-butanone, halogenated hydrocarbons, e.g. dichloromethane, and mixtures of such solvents.

The compounds of formula (I) wherein L is other than hydrogen, said L being represented by $L_a$ and said compounds being represented by formula (I-b) can be prepared by reacting the compounds of formula (I) wherein L is hydrogen, said compounds being represented by formula (I-c), with a reagent of formula $L_a$-$W_1$ (IV), wherein $W_1$ is a suitable leaving group, such as a halo atom, e.g. chloro, or mesylate, tosylate, trifluoromethanesulfonate.

TABLE 18

| Sample | Coating (%/% heptdmac/silane) | Dip | Activity, mU/cm² | | |
|---|---|---|---|---|---|
| | | | 2 days unwashed | 2 days wash | 16 days wash |
| 97-101-25A, Red | 0.1/0.5 | Double | <225 | <5 | <2 |
| 97-101-25A, Red | 0.1/0.5 | Double | <225 | 0 | <3 |
| 97-101-25B, green | 0.1/0.5 | Dip/wash/dip | <125 | <1 | <2 |
| 97-101-25B, green | 0.1/0.5 | Dip/wash/dip | <100 | 0 | <5 |
| 97-101-25C, yellow | 0.2/0.5 | Double | <200 | <15 | <3 |
| 97-101-25C, yellow | 0.2/0.5 | Double | <100 | <5 | <10 |
| 97-101-25D, brown | 0.2/0.5 | Dip/wash/dip | <200 | <5 | <10 |
| 97-101-25D, brown | 0.2/0.5 | Dip/wash/dip | <225 | <10 | <5 |

Said reaction can conveniently be conducted in a reaction-inert solvent such as, for example, an aromatic hydrocarbon, an alkanol, a ketone, an ether, a dipolar aprotic solvent, a halogenated hydrocarbon, or a mixture of such solvents. The addition of an appropriate base such as, for example, an alkali or an earth alkaline metal carbonate, hydrogen carbonate, alkoxide, hydride, amide, hydroxide or oxide, or an organic base, such as, for example, an amine, may be utilized to pick up the acid which is liberated during the course of the reaction. In some instances the addition of an iodide salt, preferably an alkali metal iodide, is appropriate. Somewhat elevated temperatures and stirring may enhance the rate of the reaction.

The compounds of formula (I-b), wherein $L_a$ is optionally substituted $C_{1-6}$alkyl, said $L_a$ being represented by $L_{a1}$ and said compounds by formula (I-b-1), can be converted into the compounds of formula (I-c) by dealkylating and subsequently carbonylating the compounds of formula (I-b-1) with a reagent of formula (V), wherein $W_2$ represents a suitable leaving group, such as a halo atom, e.g. chloro, and $L_{a2}$ represents $C_{1-6}$alkyloxycarbonyl, resulting in compounds of formula (I-b-2) and subsequently hydrolyzing the thus obtained compounds of formula (I-b-2).

The compounds of formula (I-b-2) can also be prepared by reacting compounds of formula (I-c) with a reagent of formula (V) in the presence of a suitable base, e.g. N,N-diethylethanamine, in a reaction inert solvent, e.g. methylenechloride, or by reacting compounds of formula (I-c) with a reagent of formula (VI), e.g. t-butyloxyanhydride, in a suitable solvent, such as, e.g. methylenechloride.

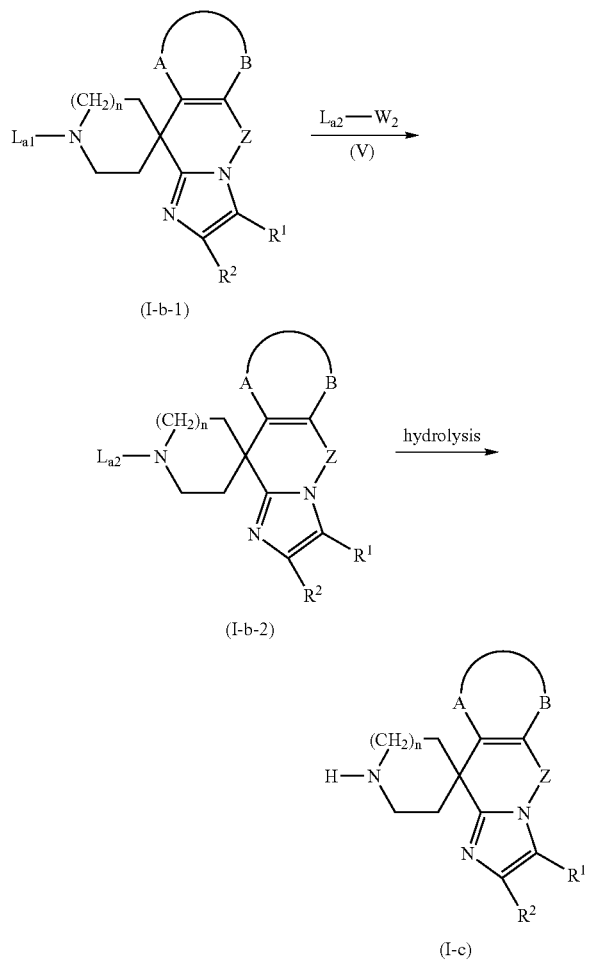

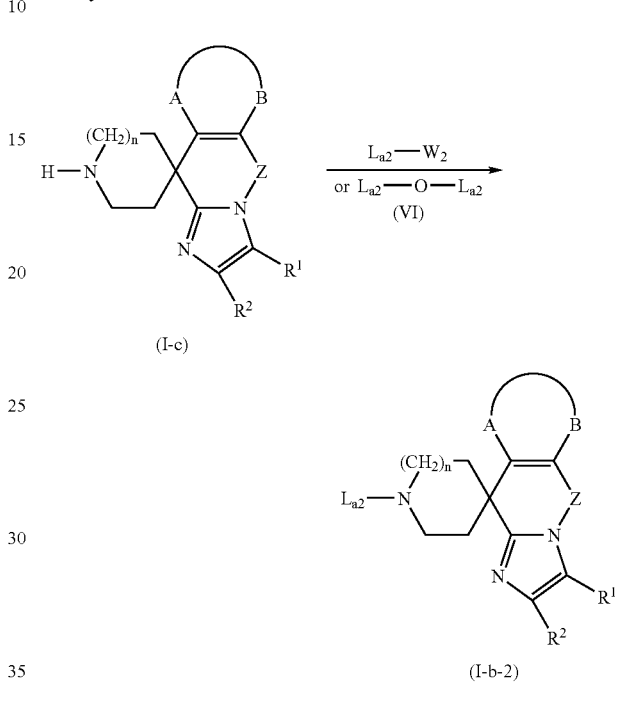

The reaction with reagent (V) is conveniently conducted by stirring and heating the starting material with the reagent in an appropriate solvent and in the presence of a suitable base. Appropriate solvents are, for example, aromatic hydrocarbons, e.g. methylbenzene, dimethylbenzene, chlorobenzene; ethers, e.g. 1,2-dimethoxyethane; methylenechloride and the like solvents. Suitable bases are, for example, alkali or earth alkaline metal carbonates, hydrogen carbonates, hydroxides, or organic bases such as, N,N-diethylethanamine, N-(1-methylethyl)-2-propanamine, and the like. The compounds of formula (I-b-2) are hydrolyzed in acidic or basic media following conventional methods. For example, concentrated acids such as hydrobromic, hydrochloric acid or sulfuric acid can be used, or alternatively bases such as alkali metal or earth alkaline metal hydroxides in water, an alkanol or a mixture of water-alkanol may be used. Suitable alkanols are methanol, ethanol, 2-propanol and the like. In order to enhance the rate of the reaction it is advantageous to heat the reaction mixture, in particular up to the reflux temperature.

The compounds of formula (I-b) wherein $R^1$ or $R^1$ and $R^2$ represent hydroxymethyl, said compounds being represented by formula (I-b-3) and (I-b-4), can be prepared by reacting the compounds of formula (I) wherein L is $L_a$ and $R^1$ and $R^2$ are hydrogen, said compounds being represented by formula (I-b-5), with formaldehyde, optionally in the presence of an appropriate carboxylic acid—carboxylate mixture such as, for example, acetic acid—sodium acetate and the like. In order to enhance the rate of the reaction, it is advantageous to heat the reaction mixture up to the reflux temperature.

The thus obtained compounds of formula (I-b-3) and (I-b-4) can be further oxidized to the corresponding aldehyde, represented by formula (I-b-6) and (I-b-7) or the corresponding carboxylic acid, represented by formula (I-b-8) and (I-b-9), by reaction with a suitable reagent such as, for example, manganese(IV)oxide, respectively, silver nitrate.

The compounds of formula (I-b-8) and (I-b-9) can further be converted in the corresponding amide, said compounds being represented by formula (I-b-10) and (I-b-11), by reaction with a suitable carbodiimide, e.g. 1-(3-dimethylaminopropyl)-3-ethylcarbodiimide, in the presence of ammonia and a suitable catalyst, e.g. N,N-dimethylaminopyridine, in a reaction inert solvent, e.g. methylenechloride.

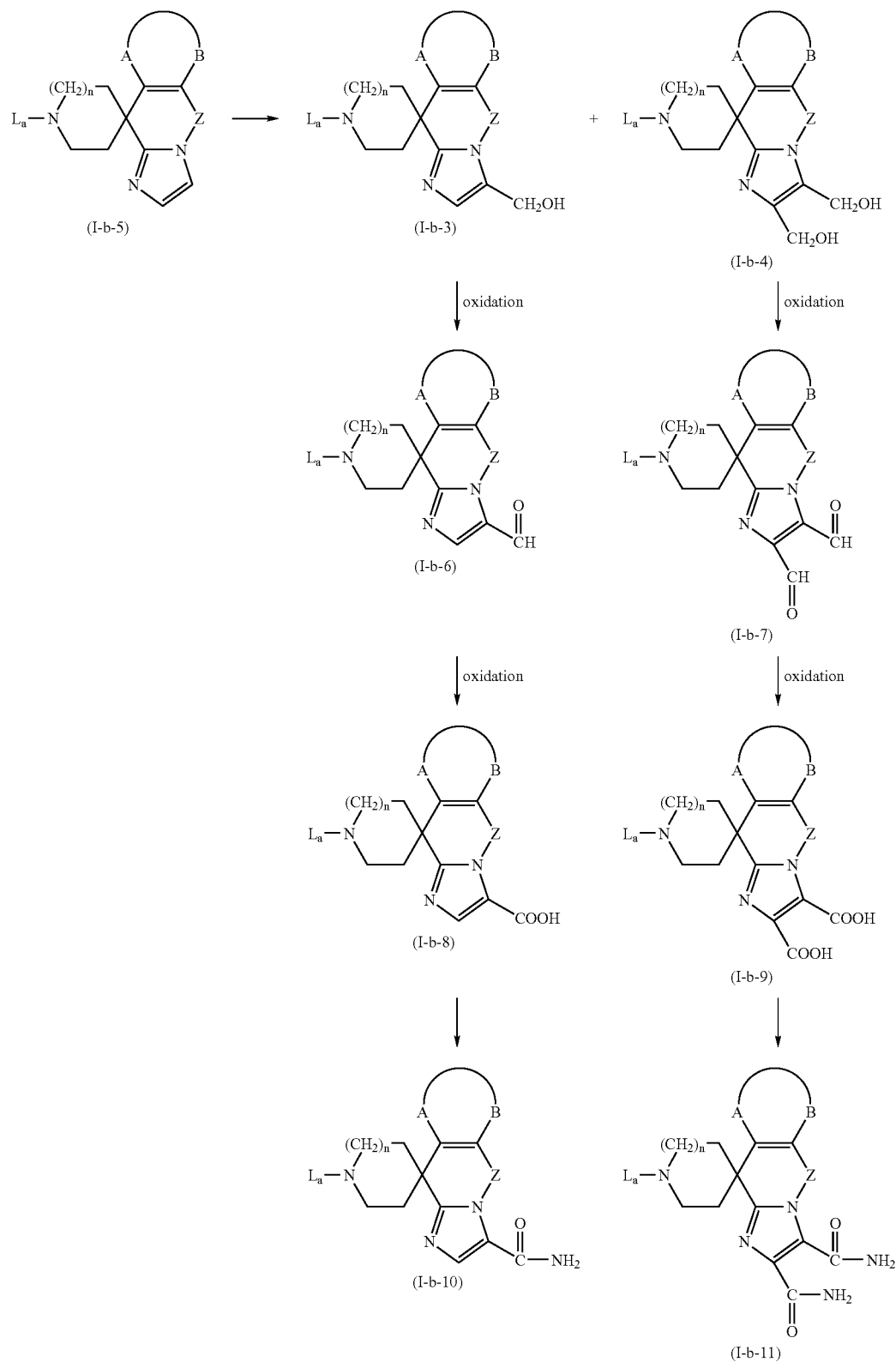

The compounds of formula (I) wherein L is $L_a$, and $R^1$ or $R^1$ and $R^2$ are halo, said compounds being represented by formula (I-b-12) and (I-b-13), can be prepared by halogenating a compound of formula (I-b-5) with an appropriate halogenating reagent in a reaction-inert solvent.

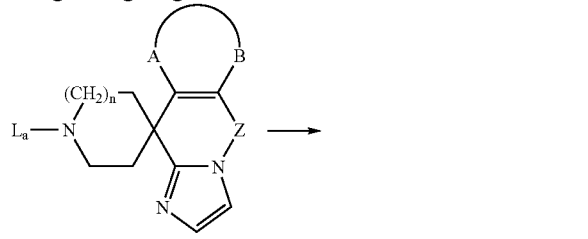

(I-b-5)

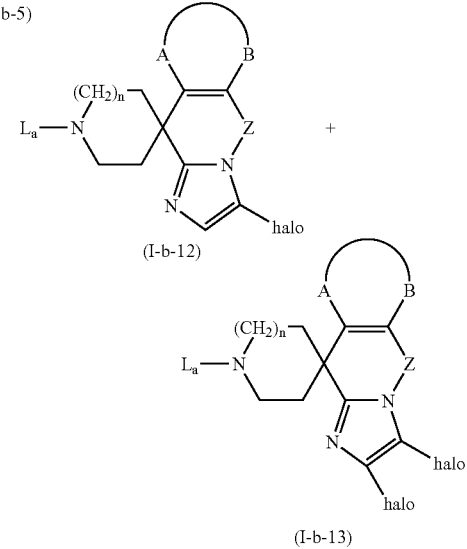

(I-b-12)

(I-b-13)

A suitable halogenating reagent in the above reaction is, for example, an N-halogenated amide, e.g. N-bromosuccinimide. A suitable reaction-inert solvent for said halogenation reaction is, for example, N,N-dimethylformamide, N,N-dimethylacetamide, methylenechloride and the like. Another suitable halogenating reagent is, for example, tetrabutylammoniumtribromide in the presence of a suitable base, e.g. sodium carbonate, in a suitable solvent, e.g. 3-methyl-2-butanone or dichloromethane/water mixture.

Compounds of formula (I-b-12) can be converted in a compound of formula (I-b-10) by reaction with CuCN in the presence of a suitable solvent, e.g. N,N-dimethylformamide/water mixture.

The compounds of formula (I-b) wherein $R^1$ is $C_{1-6}$alkyloxycarbonylethenyl, said compounds being represented by formula (I-b-14), can be prepared by reacting a compound of formula (I-b-6) with a reagent of formula (VII) in the presence of a base e.g. piperidine, pyridine, and the like.

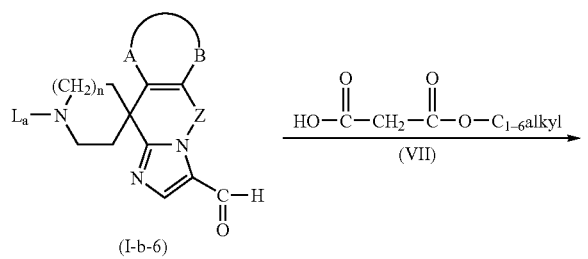

(I-b-6)          (VII)

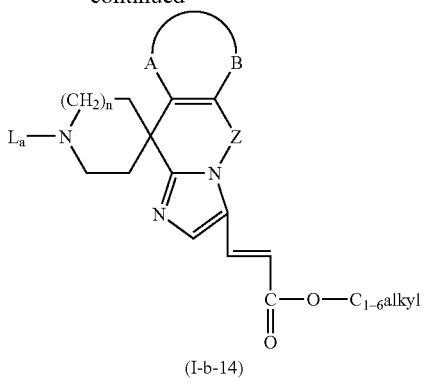

(I-b-14)

The compounds of formula (I-b-14) can further be hydrolyzed into a compound of formula (I-b) wherein $R^1$ is carboxyethenyl, in the presence of an acid or a base in case $L_a$ is $C_{1-6}$alkyl, or in the presence of a base, in case $L_a$ is $C_{1-6}$xalkyloxycarbonyl.

Compounds of formula (I-b) wherein $L_a$ is substituted ethyl, said $L_a$ being represented by $L_{a3}$—$CH_2$—$CH_2$—, and said compounds by formula (I-b-15) can be prepared by reacting a compound of formula (I-c) with a reagent of formula (VIII) in the presence of a suitable base, e.g. sodium bicarbonate or triethylamine, in a suitable reaction inert solvent, e.g. N,N-dimethylformamide or a suitable alkanol, e.g. methanol.

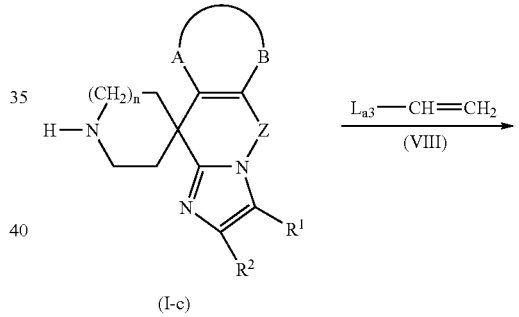

(I-c)          (VIII)

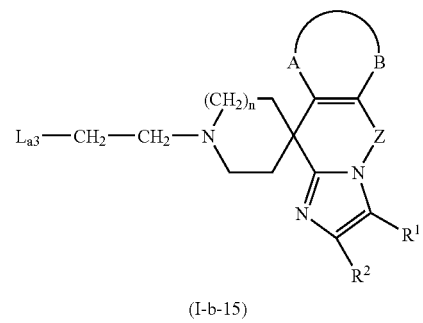

(I-b-15)

Compounds of formula (I-c) may also be converted into compounds of formula (I-b-15) wherein La3 is hydroxy, said compounds being represented by formula (I-b-15-1) by reaction with ethylene oxide in the presence of a suitable base, e.g. triethylamine, in a suitable reaction inert solvent, such as an alkanol, e.g. methanol.

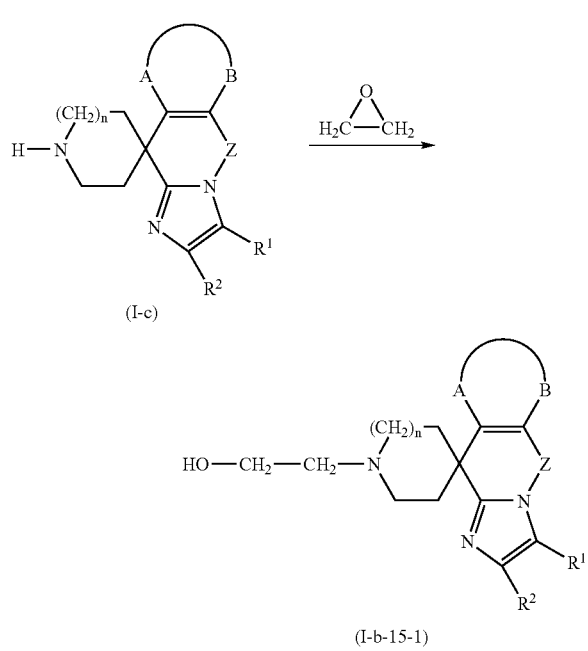

(I-c)

(I-b-15-1)

Compounds of formula (I) wherein Z is a bivalent radical of formula —CH$_2$—CHOH— (b-3), said compounds being represented by formula (I-d), can be prepared by reducing a compound of formula (I-a) in the presence of a reducing reagent, e.g. sodium borohydride, in a reaction-inert solvent, e.g. methanol and the like.

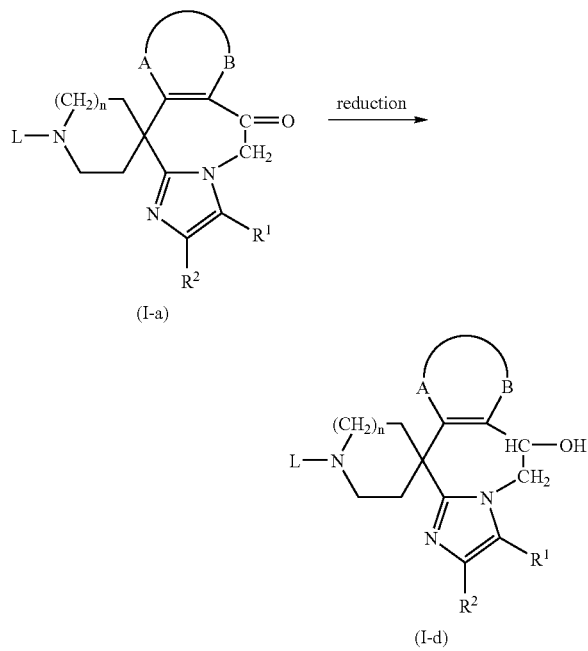

(I-a)

(I-d)

Compounds of formula (I) wherein Z is a bivalent radical of formula —CH$_2$—C(=N—OH)— (b-6), said compounds being represented by the formula (I-e), can be prepared by reacting a compound of formula (I-a) with hydroxylamine or a salt thereof, e.g. the hydrochloride salt, in a reaction inert solvent, e.g. pyridine and the like.

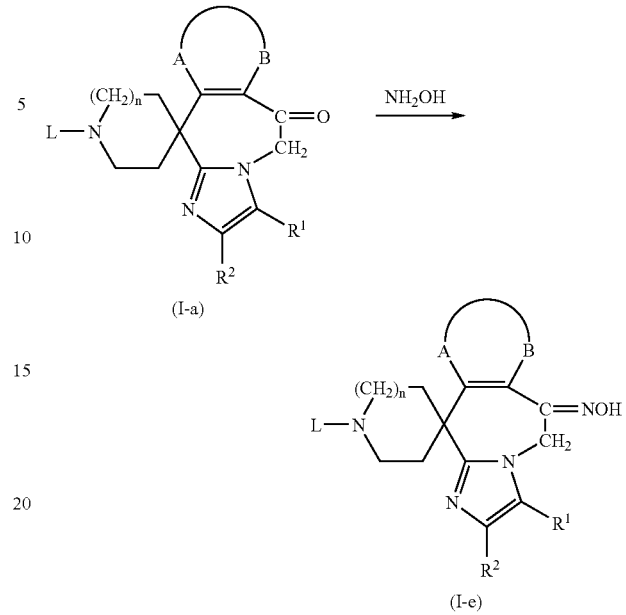

(I-a)

(I-e)

Compounds of formula (I) wherein Z is a bivalent radical of the formula —CH=CH— (b-2), said compounds being represented by formula (I-f), can be prepared by reacting a compound of formula (I-d) in the presence of an acid, e.g. methanesulfonic acid and the like.

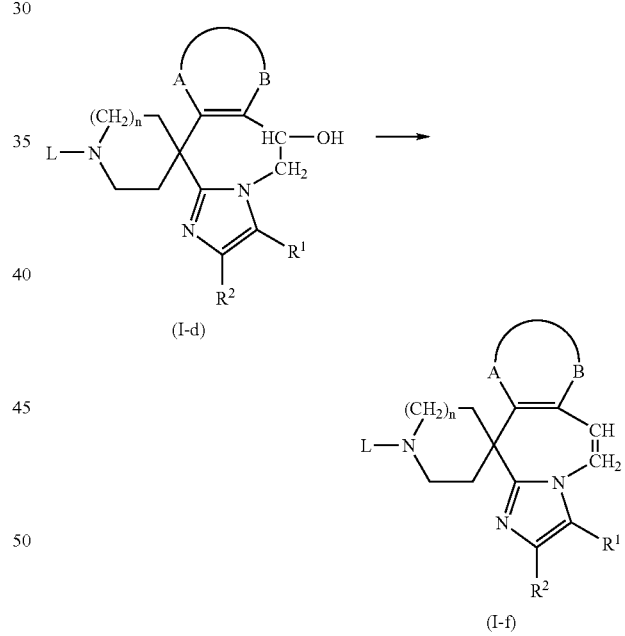

(I-d)

(I-f)

Compounds of formula (I-b) wherein L$_a$ is C$_{1-6}$alkyl substituted with C$_{1-6}$alkyloxycarbonyl or C$_{1-6}$alkyloxycarbonylNH—, can be converted into compounds of formula (I-b) wherein L$_a$ is C$_{1-6}$alkyl or aminoC$_{1-6}$alkyl by the hydrolysis reaction described above for the preparation of compounds of formula (I-c).

In the foregoing and the following preparations, the reaction mixture is worked up following art-known methods and the reaction product is isolated and, if necessary, further purified.

As described hereinabove, the intermediates of formula (II) can be derivatized at the imidazole moiety, said compounds being represented by formula (II-a), before being deprotected.

Introducing $R^1$ or $R^1$ and $R^2$ wherein $R^1$ and $R^2$ represent hydroxymethyl, formyl, carboxyl or amide, in a compound of formula (II) can be performed as described herinabove for the preparation of a compound of formula (I-b-3), (I-b-4), (I-b-6), (I-b-7), (I-b-8), (I-b-9), (I-b-10), (I-b-11).

Intermediates of formula (II-a), wherein $R^1$ is aminomethyl and $R^2$ is hydrogen, said intermediates being represented by formula (II-b), can be prepared by reacting an intermediate of formula (II-c) with hydrogen and a mixture of methanol/ammonia in the presence of a suitable catalyst, for example rhodium on aluminium, in the presence of a catalyst poison, for example a thiophene solution.

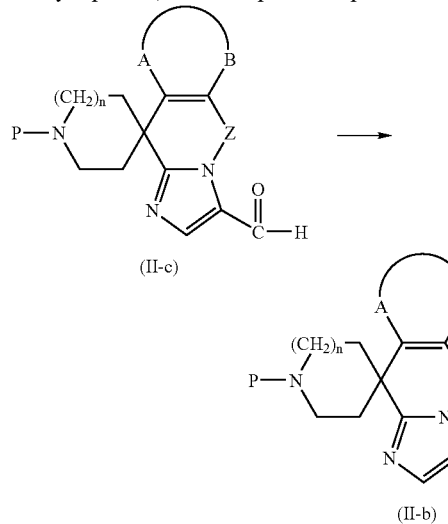

Intermediates of formula (II-a), wherein $R^1$ is —CH$_2$NHC(=O)NH$_2$ and $R^2$ is hydrogen, said intermediates being represented by formula (II-d) can be prepared by reacting an intermediate of formula (II-b) with potassium isocyanate in an appropriate acid, such as hydrochloric acid.

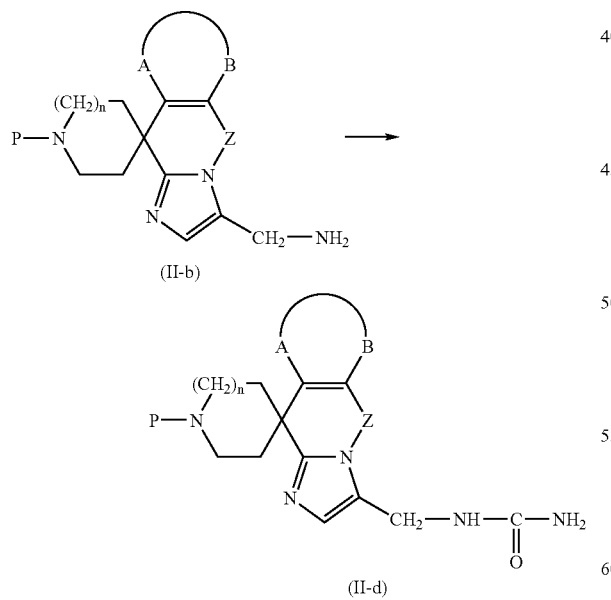

Intermediates of formula (II-b) can also be converted in an intermediate of formula (II-a), wherein $R^1$ is —CH$_2$NHC(=O)C$_{1-6}$alkyl and $R^2$ is hydrogen, said intermediate being represented by formula (II-e), by reaction with a reagent of formula (IX), wherein $W_3$ represents a suitable leaving group, such as a halo atom, for example chloro, in the presence of a suitable base, e.g. N,N-diethylethanamine, in a reaction inert solvent, such as, for example methylenechloride.

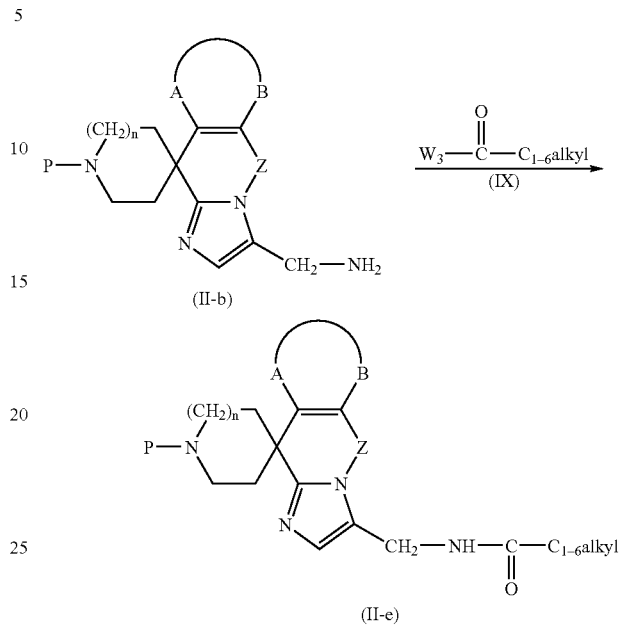

Intermediates of formula (II-b) can further be converted into an intermediate of formula (II-a), wherein $R^1$ is —CH$_2$NHS(=O)$_2$C$_{1-6}$alkyl and $R^2$ is hydrogen, said intermediate being represented by formula (II-f), by reaction with a reagent of formula (X) wherein $W_4$ represents a suitable leaving group, such as a halo atom, e.g. chloro, in the presence of a suitable base, for example N,N-diethylethanamine, in a reaction inert solvent, such as methylenechloride.

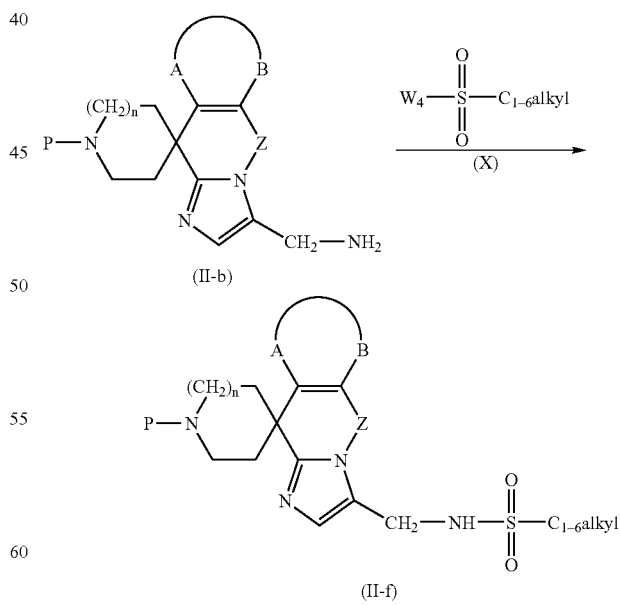

Intermediates of formula (II) can also be halogenated according to the procedure described for the preparation of the compounds of formula (I-b-12) and (I-b-13), resulting in an intermediate of formula (II-g) and (II-h).

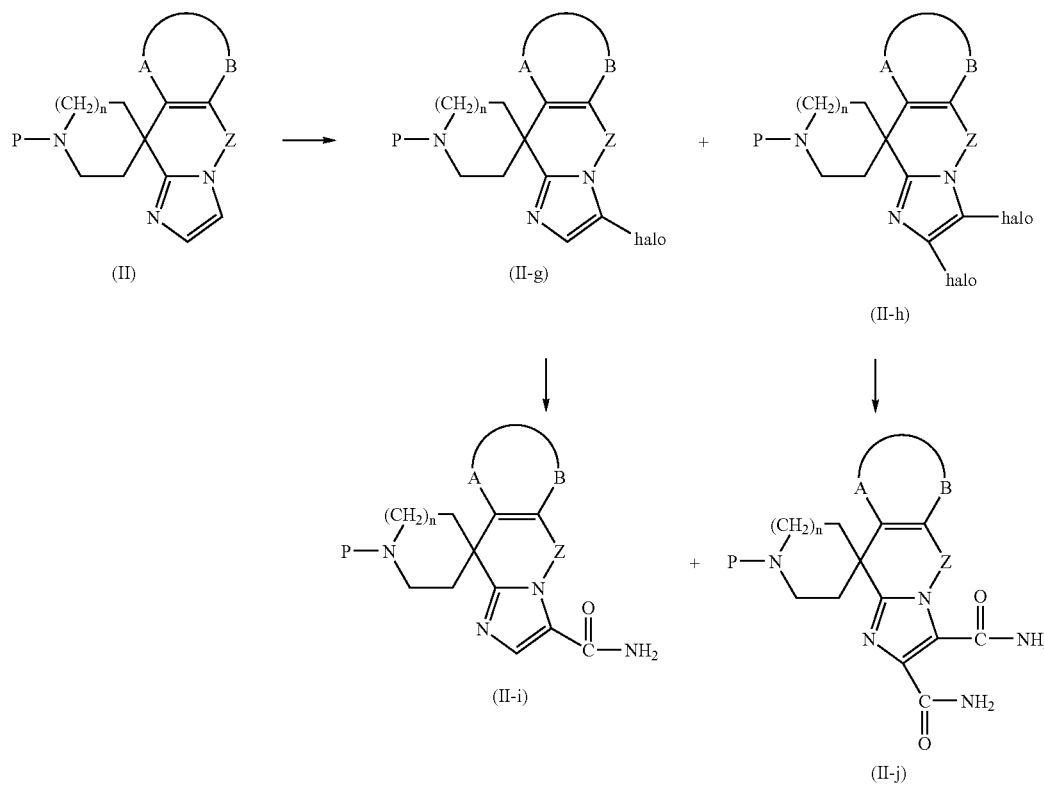

Intermediates of formula (II-g) and (II-h) can be converted in an intermediate of formula (II-i) and (II-j) by reaction under an atmosphere of ammonia and carbonmonoxide at elevated temperatures in the presence of a suitable catalyst, e.g. acetic acid, palladium salt, and a suitable ligand, e.g. 1.3-bis(diphenylphosphino)propane, in a reaction inert solvent, e.g. tetrahydrofuran.

In the following paragraphs, there are described several methods of preparing the starting materials in the foregoing preparations.

Intermediates of formula (II), wherein Z is a bivalent radical of formula —$(CH_2)_p$— (b-1), said Z being represented by $Z_1$, and said intermediates being represented by formula (II-k), can be prepared by cyclizing an alcohol of formula (XI). The intermediates of formula (II-k) may optionally be derivatized at the imidazole moiety resulting in an intermediate of formula (II-a-1) according to the procedures described for preparing a compound of formula (I-b-3), (I-b-4), (I-b-6) to (I-b-11) and an intermediate of formula (II-b) to (II-j).

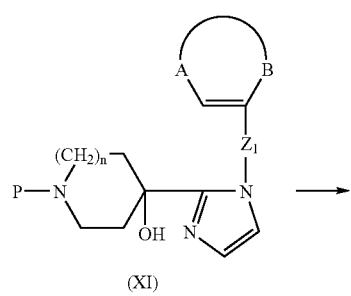

-continued

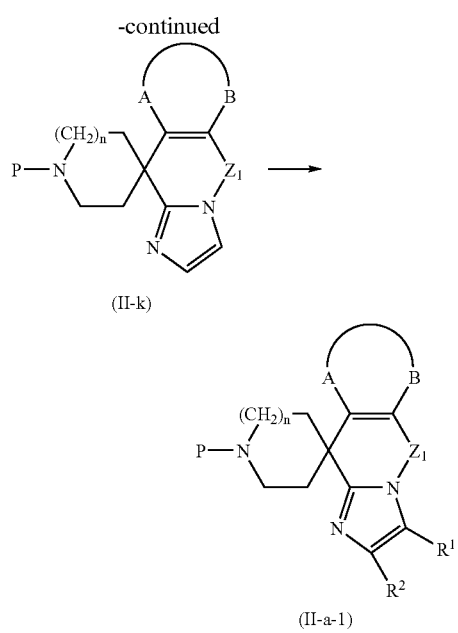

Said cyclization reaction is conveniently conducted by treating the intermediate of formula (XI) with an appropriate acid, thus yielding a reactive intermediate which cyclizes to an intermediate of formula (II-k). Appropriate acids are, for example, strong acids, e.g. methanesulfonic acid, trifluoroacetic acid, and in particular superacid systems, e.g. trifluoromethanesulfonic acid, or Lewis acids, such as $AlCl_3$ or $SnCl_4$. Obviously, only those compounds of formula II wherein P is stable under the given reaction conditions can be prepared according to the above reaction procedure.

Intermediates of formula (XI) can be prepared by reacting an imidazole derivative of formula (XII) with a ketone of formula (XIII).

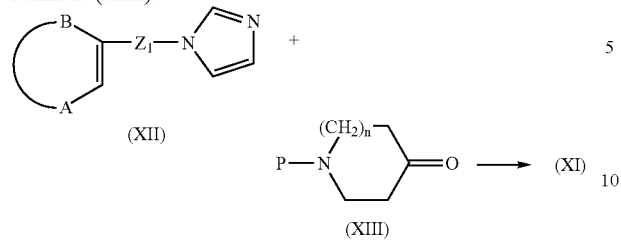

Said reaction is conveniently performed in a reaction inert solvent such as, for example tetrahydrofuran, in the presence of a suitable base such as lithium diisopropylamide and butyl lithium.

Intermediates of formula (II), wherein Z represents a bivalent radical of formula —$(CH_2)_p$— (b-1), or —$CH_2$—O— (b-4), said Z being represented by $Z_2$, and said intermediates being represented by formula (II-l), can also be prepared by reacting a tricyclic moiety of formula (XIV) with a reagent of formula (XV), wherein $W_5$ represents a suitable leaving group, e.g. a halo atom, such as chloro, under an inert atmosphere in a reaction inert solvent, such as tetrahydrofuran, in the presence of a suitable base such as, for example, lithium diisopropylamide and butyl lithium. The intermediates of formula (II-l) may optionally be derivatized at the imidazole moiety resulting in an intermediate of formula (II-a-2) according to the procedures described for preparing a compound of formula (I-b-3), (I-b-4), (I-b-6) to (I-b-11) and an intermediate of formula (II-b) to (II-j).

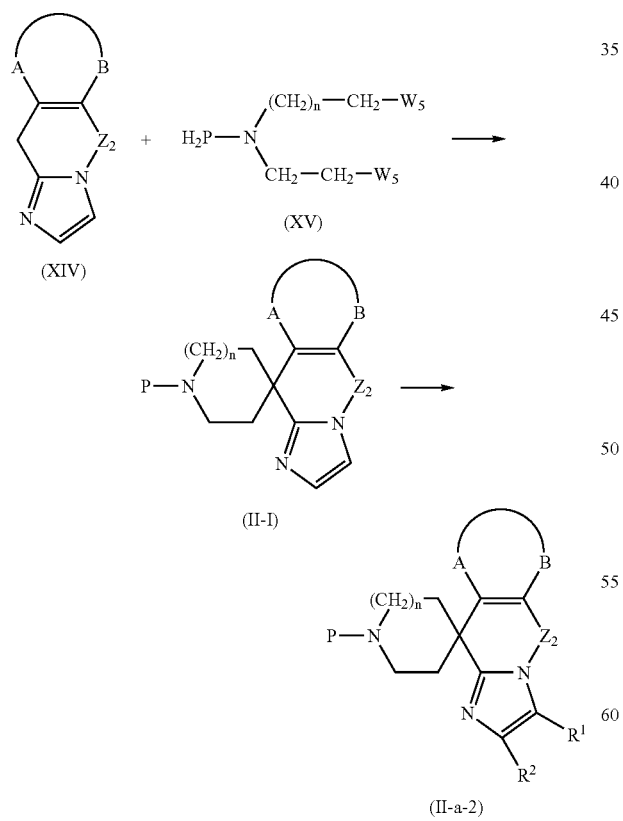

Intermediates of formula (XIV) can be prepared by cyclizing an intermediate of formula (XVI), according to the procedure described for the preparation of intermediates of formula (II-k).

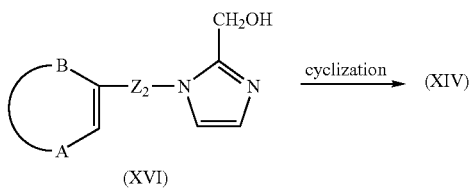

Intermediates of formula (XVI) can be prepared by reduction from the corresponding aldehydes, said intermediates being represented by formula (XVII).

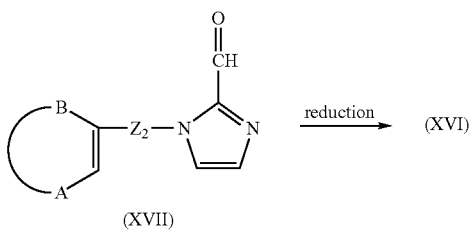

Said reduction can be conducted in a suitable solvent, such as, for example methanol, in the presence of a suitable reducing agent, such as sodium borohydride.

Intermediates of formula (XVI) can also be prepared by reacting an intermediate of formula (XVIII) with formol 38% solution under pressure.

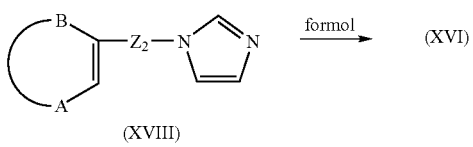

Alternatively, the tricyclic moieties of formula (XIV), wherein Z represents a bivalent radical of formula —$CH_2$—, said Z being represented by $Z_3$, and said tricylclic moieties being represented by formula (XIV-a), may also be prepared by first cyclizing an intermediate of formula (XVII) wherein $Z_2$ represents $Z_3$, said intermediate being represented by formula (XVII-a), by treating said intermediate with an appropriate acid, e.g. trifluoroacetic acid, leading to an intermediate of formula (XIX), followed by reduction in the presence of a suitable reducing agent.

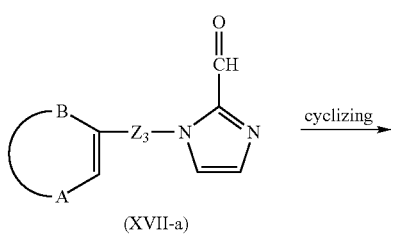

Intermediates of formula (XXII) can be prepared by imidazole formation out of an intermediate of formula (XXIII) in an acid, such as hydrochloric acid.

(XXIII)

Intermediates of formula (XXII) can be prepared by reacting an intermediate of formula (XXIV) with 2,2-dimethoxyethylamine in a reaction inert solvent, such as, for example N,N-dimethylformamide and the like.

(XXIV)   (XXIII)

Intermediates of formula (XXIV) can be prepared by reacting an intermediate of formula (XXV) with thionyl-chloride.

$\xrightarrow{SOCl_2}$ (XXIV)

(XXV)

Intermediates of formula (XXV) can be prepared by substituting an intermediate of formula (XXVI) with benzylamine in the presence of a suitable base, e.g. N,N-diethylethanamine, in a reaction inert solvent, e.g. methylenechloride and the like.

(XXVI)

Pure stereochemically isomeric forms of the compounds of formula (I) may be obtained by the application of art-known procedures. Diastereomers may be separated by physical methods such as selective crystallization and chromatographic techniques, e.g., counter-current distribution, liquid chromatography and the like.

The compounds of formula (I) as prepared in the hereinabove described processes are generally racemic mixtures of enantiomers which can be separated from one another following art-known resolution procedures. The racemic compounds of formula (I) which are sufficiently basic or acidic may be converted into the corresponding diastereomeric salt forms by reaction with a suitable chiral acid, respectively chiral base. Said diastereomeric salt forms are subsequently separated, for example, by selective or fractional crystallization and the enantiomers are liberated therefrom by alkali or acid. An alternative manner of separating the enantiomeric forms of the compounds of formula (I) involves liquid chromatography, in particular liquid chromatography using a chiral stationary phase. Said pure stereochemically isomeric forms may also be derived from the corresponding pure stereochemically isomeric forms of the appropriate starting materials, provided that the reaction occurs stereospecifically. Preferably if a specific stereoisomer is desired, said compound will be synthesized by stereospecific methods of preparation. These methods will advantageously employ enantiomerically pure starting materials.

A number of intermediates and starting materials are commercially available or are known compounds which may be prepared according to conventional reaction procedures generally known in the art. For example, the preparation of 1-(1-phenylethyl)-1H-imidazole is described in WO 92/22551.

The compounds of formula (I), their prodrugs, N-oxides, addition salts, quaternary amines and stereochemically isomeric forms possess useful pharmacological properties. In particular they are active antihistaminic agents, which activity can be demonstrated by for instance the 'Histamine—induced Lethality in Guinea Pigs' test (Arch. Int. Pharmacodyn. Ther., 251, 39–51, 1981), 'Protection of Rats from Compound 48/80-induced Lethality' test (Arch. Int. Pharmacodyn. Ther., 234, 164–176, 1978), and 'Ascaris Allergy in Dogs' test (Arch. Int. Pharmacodyn. Ther., 251, 39–51, 1981 and Drug Dev. Res., 8, 95–102,1986).

Some of the intermediates of formula (II-a) also have interesting pharmacological properties.

The compounds of the present invention have a selective binding affinity for the $H_1$ receptor, more in particular, they have a very low affinity for the $5HT_{2A}$ serotonin receptor and the $5HT_{2C}$ serotonin receptor. This dissociation between the $H_1$ receptor binding affinity and the $5HT_{2C}$ and $5HT_{2A}$ receptor binding affinity renders it unlikely for the present compounds to cause appetite stimulation and inappropriate weight gain reported for some other $H_1$-antagonists.

An important asset of the present compounds is their lack of sedating properties at therapeutic dose levels, a troublesome side effect associated with many antihistaminic and antiallergic compounds. The non-sedating properties of the present compounds can be demonstrated, for example, by the results obtained in studying the sleep—wakefulness cycle of the rat (Psychopharmacology, 97, 436–442, (1989)) and the state of vigilance using EEG power spectra in wake rats (Sleep Research 24A, 118, (1995)).

The compounds of the present invention are also characterized by the absence of relevant cardio-hemodynamic and electrophysiological effects such as QTc prolongation.

An additional advantage of some of the present compounds is that they exhibit little or no metabolic transformations in animal and human liver, thus indicating a low risk for metabolic interactions.

Another interesting feature of the present compounds relates to their fast onset of action and the favorable duration of their action. The latter characteristic may enable the administration of the compound once daily.

The present compounds have a favorable physicochemical profile, particularly in terms of solubility and chemical stability.

In view of their physicochemical and pharmacological properties, the compounds of formula (I), their prodrugs, N-oxides, addition salts, quaternary amines and stereochemically isomeric forms thereof are very useful in the treatment of a broad range of allergic diseases such as, for example, allergic rhinitis, allergic conjunctivitis, chronic urticaria, pruritis, allergic asthma and the like.

Also in view of their useful physicochemical and pharmacological properties the subject compounds may be formulated into various pharmaceutical forms for administration purposes. To prepare the antiallergic compositions of this invention, an effective amount of the particular compound, in base or acid addition salt form, as the active ingredient is combined in intimate admixture with a pharmaceutically acceptable carrier, which carrier may take a wide variety of forms depending on the form of preparation desired for administration. These pharmaceutical compositions are, desirably as unitary dosage forms, administered orally, parenterally, percutaneously, rectally or topically for systemic action, or for topical action. In case of oral liquid pharmaceutical preparations, comprising solutions, suspensions, syrups, elixirs and emulsions, any of the usual pharmaceutical media, such as, for example, water, glycols, oils, alcohols and the like, may be employed, whereas in case of oral solid pharmaceutical preparations, comprising powders, pills, capsules and tablets, excipients such as starches, sugars, kaolin, lubricants, binders, disintegrating agents and the like may be employed. Because of their ease in administration, tablets and capsules represent the most advantageous oral unit dosage forms, in which case solid pharmaceutical carriers are obviously employed. In case of injectable pharmaceutical compositions, the carrier will usually comprise sterile water, at least in large part, though other ingredients, such as semipolair solvents, may be included, for example, to aid solubility. Examples of carriers for injectable solutions comprise saline solution, glucose solution or a mixture of saline and glucose solution. Injectable solutions containing compounds of the aforementioned formulas may also be formulated in an oil for prolonged action. Appropriate oils for this purpose are, for example, peanut oil, sesame oil, cottonseed oil, corn oil, soy bean oil, synthetic glycerol esters of long chain fatty acids and mixtures of these and other oils. For the preparation of injectable suspensions, appropriate liquid carriers, suspending agents and the like may be employed. In the compositions suitable for percutaneous administration, the carrier optionally comprises a penetration enhancing agent and/or a suitable wettable agent, optionally combined with suitable additives of any nature in minor proportions, which additives do not cause any significant deleterious effects on the skin. Said additives may facilitate the administration to the skin and/or may be helpful for preparing the desired compositions. These compositions may be administered in various ways, e.g., as a transdermal patch, as a spot-on, as an ointment or as a gel. In case of pharmaceutical compositions for rectal administration, any of the usual excipients may be employed, comprising fat based and water soluble excipients, optionally combined with suitable additives, such as suspending or wetting agents. As appropriate compositions for topical application there may be cited all compositions usually employed for topically administering drugs e.g. creams, gellies, dressings, lotions, shampoos, tinctures, pastes, ointments, salves, ovules, powders, inhalations, nose sprays, eye drops and the like. Semisolid compositions such as salves, creams, gellies, ointments and the like will conveniently be used, but application of said compositions may be, for example, also by aerosol, e.g. with a propellent such as nitrogen, carbon dioxide, a freon, or without a propellent such as a pump spray or drops.

It is especially advantageous to formulate the aforementioned pharmaceutical compositions in unit dosage form for ease of administration and uniformity of dosage. Unit dosage form as used in the specification and claims herein refers to physically discrete units suitable as unitary dosages, each unit containing a predetermined quantity of active ingredient calculated to produce the desired therapeutic effect in association with the required pharmaceutical carrier. Examples of such unit dosage forms are tablets (including scored or coated tablets), capsules, pills, powder packets, suppositories, ovules, wafers, injectable solutions or suspensions, teaspoonfuls, tablespoonfuls and the like, and segregated multiples thereof.

The present invention also relates to a method of treating warm-blooded animals suffering from allergic diseases by administering to said warm-blooded animals an effective anti-allergic amount of a compound of formula (I), a prodrug, N-oxide, addition salt, quaternary amine or stereochemically isomeric form thereof.

The present invention further relates to the compounds of formula (I), their prodrugs, N-oxides, addition salts, quaternary amines and stereochemically isomeric forms thereof for use as a medicine, and hence, the use of the present compounds for the manufacture of a medicament for treating warm-blooded animals suffering from allergic diseases is also part of the present invention.

In general it is contemplated that an effective antiallergic amount would be from about 0.001 mg/kg to about 2 mg/kg body weight, and more preferably from about 0.01 mg/kg to about 0.5 mg/kg body weight. In any event, an effective antiallergic amount may depend on the type and severity of the affliction to be treated and the evaluation of the physician prescribing the treatment with the subject drugs.

The following examples are intended to illustrate the scope of the present invention.

EXPERIMENTAL PART

Hereinafter, THF means tetrahydrofuran, DIPE means diisopropyl ether, DMF means N,N-dimethylformamide, DIPA means diisopropyl amine
A. Preparation of Intermediate Compounds

EXAMPLE A1 a) A mixture of DIPA (1.4 mol) in THF (3000 ml) was stirred at −70° C. under $N_2$ flow. Butyllithium 2.5 M/hexane (1.3 mol) was added portionwise at a temperature below −40° C. The mixture was stirred at −70° C. for 15 min. 1-phenylethyl-1H-imidazole (1 mol) dissolved in THF was added dropwise at a temperature below −55° C. The mixture was stirred at −70° C. for 1 hour. 1-(phenylmethyl)-4-piperidinone (1.2 mol) dissolved in THF was added dropwise at a temperature below −55° C. The mixture was stirred at −70° C. for 1 hour, then brought to room temperature, stirred at room temperature overnight and decomposed with $H_2O$. The organic solvent was evaporated. The aqueous concentrate was extracted with $CH_2Cl_2$. The organic layer was separated, dried ($MgSO_4$), filtered and the solvent was evaporated. The residue was crystallized from DIPE (1100 ml). The precipitate was filtered off, washed with DIPE and dried, yielding 271 g of 4-[1-(2-phenylethyl)-1H-imidazol-2-yl]-1-(phenylmethyl)-4-piperidinol (75%) (interm. 1).

b) A mixture of intermediate (1) (0.75 mol) in trifluoromethanesulfonic acid (1500 ml) was stirred at 65° C. for 120 hours, then cooled, poured out on ice, alkalized with NaOH 50% and extracted with $CH_2Cl_2$. The organic layer was separated, dried ($MgSO_4$), filtered and the solvent was evaporated. The residue was crystallized from DIPE/$CH_3CN$ (99/1) (1200 ml). The precipitate was filtered off and dried, yielding 169.6 g of 5,6-dihydro-1'-(phenylmethyl)spiro[11H-imidazo[2,1-b][3]benzazepine-11,4'-piperidine] (66%) (interm. 2).

EXAMPLE A2

1-(phenylmethyl)-4-[1-(phenylmethyl)-1H-imidazol-2-yl]-4-piperidinol (0.124 mol) and $AlCl_3$ (0.31 mol) were stirred in a melt at 120° C. for 1 h. The mixture was cooled, $AlCl_3$ (0.31 mol) was added and the mixture was stirred at 120° C. for 1 h. The mixture was poured into ice, alkalized with NaOH 50% and extracted with $CH_2Cl_2$. The organic layer was dried ($MgSO_4$), filtered off and evaporated. The residue was purified by HPLC (eluent: $CH_2Cl_2$/($CH_3OH$/$NH_3$)99/1). The pure fractions were collected and evaporated. The residue was converted into the hydrochloric acid salt (1:2) in $(C_2H_5)_2O$, yielding 0.91 g of 1'-(phenylmethyl)spiro[imidazo[1,2-b]isoquinoline-10[5H],4'-piperidine] dihydrochloride.dihydrate (2%) (interm. 3; mp. 161.2° C.).

EXAMPLE A3 a) A mixture of intermediate (2) (0.09 mol) in $CH_2Cl_2$ (1000 ml) was cooled to 0° C. 1-bromo-2,5-pyrrolidinedione (0.09 mol) was added portionwise over a 1-hour period. The organic layer was separated, washed with $H_2O$, dried, filtered and the solvent was evaporated. The residue was purified by column chromatography over silica gel (eluent: $CH_2Cl_2$/$CH_3OH$ 97.5/2.5 to 95/5). A pure fraction was collected and the solvent was evaporated. The residue was dissolved in ethanol and converted into the (E)-2-butenedioic acid salt (1:1). The precipitate was filtered off and dried, yielding 17.3 g of 3-bromo-5,6-dihydro-1'-(phenylmethyl)spiro[11H-imidazo[2,1-b][3]-benzazepine-11,4'-piperidine (E)-2-butenedioate (1:1) (36%) (interm. 4). Part of this fraction (16.5 g) was taken up in $H_2O$, $K_2CO_3$ and $CH_2Cl_2$. The mixture was separated into its layers. The aqueous layer was extracted with $CH_2Cl_2$. The combined organic layer was dried (MgSO4), filtered and the solvent was evaporated, yielding 12.9 g of 3-bromo-5,6-dihydro-1'-(phenylmethyl)spiro[11H-imidazo[2,1-b][3]benzazepine-11,4'-piperidine (interm. 4a).

b) A mixture of intermediate (4a) (0.21 mol), 1,3-propanediylbis[diphenylphosphine] (2.5 g) and acetic acid, palladium(2+) salt (0.68 g) in THF (567 ml) was stirred in an autoclave at 150° C. for 16 hours under $NH_3$ (10 atm) and CO (30 atm). The mixture was filtered and the filtrate was evaporated. This residue was purified by column chromatography over silica gel (eluent: $CH_2Cl_2$/$C_2H_5OH$ 100/0 over 46 min to 70/30). The pure fractions were collected and the solvent was evaporated, yielding 36 g of 5,6-dihydro-1'-(phenylmethyl)spiro[11H-imidazo[2,1-b][3]benzazepine-11,4'-piperidine]-3-carboxamide (44%) (interm. 5).

EXAMPLE A4 a) A mixture of intermediate (2) (0.16 mol) and sodium acetate (45 g) in formol 38% (300 ml) and acetic acid (30 ml) was stirred and refluxed for 6 hours, then cooled, poured out on ice and alkalized with a NaOH solution. The precipitate was filtered off and purified by column chromatography over silica gel (eluent: $CH_2Cl_2/CH_3OH$ 99/1). The desired fractions were collected and the solvent was evaporated. The residue was triturated in $CH_3CN$, filtered off and dried, yielding 13 g of 5,6-dihydro-1'-(phenylmethyl)spiro[11H-imidazo[2,1-b][3]benzazepine-11,4'-piperidine]-3-methanol (interm. 6).

b) A mixture of intermediate (6) (0.032 mol) and $MnO_2$ (65 g) in chloroform (250 ml) was stirred and refluxed for 2 hours, then cooled, filtered over dicalite and the filtrate was evaporated, yielding 11 g of 5,6-dihydro-1'-(phenylmethyl)spiro[11H-imidazo-[2,1-b][3]benzazepine-11,4'-piperidine]-3-carboxaldehyde (interm. 7).

c) A mixture of intermediate (7) (0.0296 mol) in $CH_3OH/NH_3$ (500 ml) was hydrogenated at 50° C. with $Rh/Al_2O_3$ 5% (2 g) as a catalyst in the presence of a thiophene solution (2 ml). After uptake of $H_2$ (1 equiv), the catalyst was filtered off and the filtrate was evaporated, yielding 11 g of 5,6-dihydro-1'-(phenylmethyl)spiro[11H-imidazo[2,1-b][3]benzazepine-11,4'-piperidine]-3-methanamine (interm. 8). Part of this fraction (1 g) was purified by column chromatography over silica gel (eluent: $CH_2Cl_2/(CH_3OH/NH_3)$ 95/5). The pure fractions were collected and the solvent was evaporated. The residue was dissolved in 2-propanol and converted into the hydrochloric acid salt (1:3) with 2-propanol/HCl. The mixture was crystallized from DIPE. The precipitate was filtered off and dried, yielding 0.8 g of 5,6-dihydro-1'-(phenylmethyl)spiro[11H-imidazo[2,1-b][3]benzazepine-11,4'-piperidine]-3-methanamine hydrochloride (1:3) hydrate (1:1) (interm. 8a).

d) A mixture of intermediate (8) (0.0198 mol) in HCl 1N (50 ml) was stirred at 50° C. KOCN (0.023 mol) was added portionwise (4×0.5 g). The mixture was stirred at 50° C. for 2 hours, then cooled, neutralized with a $NaHCO_3$ solution and extracted with $CH_2Cl_2$. The organic layer was separated, washed with $H_2O$, dried, filtered and the solvent was evaporated. The residue was purified by column chromatography over silica gel (eluent: $CH_2Cl_2/(CH_3OH/N_3)$ 95/5). The pure fractions were collected and the solvent was evaporated, yielding 4.3 g of N-[[5,6-dihydro-1'-(phenylmethyl)spiro-[11H-imidazo[2,1-b][3]benzazepin]-3-yl]methyl]methyl]urea (interm. 9).

EXAMPLE A5

A mixture of intermediate (8) (0.0295 mol) and triethylamine (0.035 mol) in $CH_2Cl_2$ (140 ml) was stirred at room temperature. A solution of acetyl chloride (0.03 mol) in $CH_2Cl_2$ (10 ml) was added dropwise. The mixture was stirred at room temperature for 1 hour and poured out into $H_2O$. $K_2CO_3$ (2 g) was added. The mixture was extracted with $CH_2Cl_2$. The organic layer was separated, washed with $H_2O$, dried, filtered and the solvent was evaporated. The residue was purified by column chromatography over silica gel (eluent: $CH_2Cl_2/CH_3OH$ 97/3). The pure fractions were collected and the solvent was evaporated. Part of the residue (1.3 g) was purified by column chromatography over silica gel (eluent: $CH_2Cl_2/CH_3OH$ 95/5). The pure fractions were collected and the solvent was evaporated. The residue was triturated in DIPE, filtered off and dried, yielding N-[[5,6-dihydro-1'-(phenylmethyl)spiro[11H-imidazo[2,1-b][3]-benzazepine-11,4'-piperidin]-3-yl]methyl]acetamide (interm. 10).

EXAMPLE A6

A mixture of intermediate (8) (0.012 mol) and triethyl amine (0.015 mol) in $CH_2Cl_2$ (150 ml) was stirred at 0° C. under $N_2$ flow. Methanesulfonyl chloride (0.013 mol) was added dropwise. The mixture was stirred for 2 hours. $H_2O$ was added and the mixture was extracted with $CH_2Cl_2$. The organic layer was separated, washed with $H_2O$, dried, filtered and the solvent was evaporated. The residue was purified by column chromatography over silica gel (eluent: $CH_2Cl_2/CH_3OH$ 98/2). The pure fractions were collected and the solvent was evaporated, yielding 2.1 g of N-[[5,6-dihydro-1'-(phenylmethyl)spiro[11H-imidazo[2,1-b][3]benzazepine-11,4'-piperidin]-3-yl]methyl]methanesulfonamide (interm. 11).

EXAMPLE A7 a) 1-Methyl-4-phenyl-4-piperidinecarbonyl chloride (0.49 mol) was added portionwise at room temperature to a stirring mixture of benzenemethanamine (0.49 mol) and triethyl amine (1.223 mol) in $CH_2Cl_2$ (2500 ml). The mixture was stirred at room temperature for 1 hour. $K_2CO_3$ (150 g) and $H_2O$ were added. The mixture was stirred and separated into its layers. The aqueous layer was extracted with $CH_2Cl_2$. The combined organic layer was dried ($MgSO_4$), filtered and the solvent was evaporated, yielding 144 g of 1-methyl-4-phenyl-N-(phenylmethyl)-4-piperidinecarboxamide (95%) (interm. 12).

b) A mixture of intermediate (12) (0.47 mol) in thionylchloride (750 ml) was stirred and refluxed for 1 hour. The solvent was evaporated. Toluene was added twice and evaporated again, yielding 190 g of N-[chloro(1-methyl-4-phenyl-4-piperidinyl)-methylene]benzenemethanamine monohydrochloride (100%) (interm). 13).

c) A mixture of intermediate (13) (0.47 mol) in DMF (750 ml) was cooled on an ice bath. 2,2-Dimethoxyethanamine (0.54 mol) dissolved in DMF was added dropwise. The mixture was stirred at room temperature overnight. The solvent was evaporated, yielding 210 g of N-(2,2-dimethoxyethyl)-1-methyl-4-phenyl-N'-(phenylmethyl)-4-piperidinecarboximidamide dihydrochloride (100%) (interm. 14).

d) A mixture of intermnediate (14) (0.47 mol) in HCl 6N (1500 ml) was stirred until a cloudy solution, then washed with $CH_2Cl_2$ (900 ml), stirred at 80° C. for 1 hour, cooled, alkalized with a NaOH 50% solution and extracted with $CH_2Cl_2$. The organic layer was separated, dried ($MgSO_4$), filtered and the solvent was evaporated. The residue was crystallized from $CH_3CN$. The precipitate was filtered off and dried, yielding 38.3 g of 1-methyl-4-phenyl-4-[1-(phenylmethyl)-1H-imidazol-2-yl]piperidine (25%) (interm. 15).

e) A mixture of intermediate (15) (0.195 mol) in methanol (350 ml) was hydrogenated at room temperature for 18 hours with palladium on charcoal 10% (3 g) as a catalyst. After uptake of $H_2$ (1 equiv), the catalyst was filtered off and the filtrate was evaporated. The residue was crystallized from $CH_3CN$. The precipitate was filtered off and dried, yielding 42.3 g of 4-(1H-imidazol-2-yl)-1-methyl-4-phenylpiperidine (90%) (interm. 16).

f) A mixture of sodium hydride 60% (0.232 mol) in DMF (150 ml) was stirred at room temperature. Intermediate (16) (0.145 mol) dissolved in DMF (400 ml) was added dropwise. The mixture was stirred at room temperature for 1 hour. Methyl 2-chloroacetate (0.232 mol) dissolved in DMF (400 ml) was added dropwise. The mixture was stirred at room temperature for 20 min, poured out into a solution of NaHCO$_3$ (20 g) in H$_2$O (2000 ml) and extracted with CH$_2$Cl$_2$. The organic layer was separated, dried (MgSO$_4$), filtered and the solvent was evaporated. The residue was purified by column chromatography over silica gel (eluent: CH$_2$Cl$_2$/(CH$_3$OH/NH$_3$) 95/5). The pure fractions were collected and the solvent was evaporated, yielding 40.1 g of methyl 2-(1-metyl-4-phenyl-4-piperidinyl)-1H-imidazole-1-acetate (88%) (interm. 17).

EXAMPLE A8 a) Reaction under N$_2$ atmosphere. A mixture of DIPA (0.455 mol) in THF (500 ml) was stirred at −78° C. Butyllithium, 2.5M/hexane (0.390 mol) was added dropwise at −40° C. The mixture was stirred for 15 min, then re-cooled to −78° C. A solution of 1-(4-phenylbutyl)-1H-imidazole, prepared according to the procedure described in J. Chem. Soc., Perkin Trans., 1 (1975), 17, 1670–1671, (0.325 mol) in THF (350 ml) was added dropwise at −60° C. The mixture was stirred for one hour, then re-cooled to −78° C. This mixture was added dropwise to a mixture of N,N-dimethylformamide (0.390 mol, dry, p.a.) in THF (500 ml), stirred at −78° C. The reaction mixture was stirred for one hour at −78° C., then allowed to warm to room temperature while stirring overnight. A saturated aqueous NH$_4$Cl solution (400 ml) was added and this mixture was extracted with THF. The separated organic layer was dried, filtered and the solvent evaporated, yielding 74.2 g of 1-(4-phenylbutyl)-1H-imidazole-2-carboxamide (interm. 18).

b) A mixture of intermediate (18) (0.325 mol) in methanol (1400 ml) was stirred at room temperature. NaBH$_4$ (0.650 mol) was added portionwise and the reaction mixture was stirred for 2 hours at room temperature. The solvent was evaporated. The residue was taken up into water and this mixture was extracted with CH$_2$Cl$_2$. The separated organic layer was dried, filtered and the solvent evaporated. The residue was purified by column chromatography over silica gel (eluent: CH$_2$Cl$_2$/CH$_3$OH 100/0, 99/1, 97/3, 96/4, 95/5 and 93/7). The desired fractions were collected and the solvent was evaporated, yielding 49.5 g of 1-(4-phenylbutyl)-1H-imidazole-2-methanol (66%) (interm. 19).

c) A mixture of intermediate (19) (0.417 mol) in methanesulfonic acid (960 ml) was stirred at 120° C. for 40 hours, then cooled, poured out on ice and alkalized with NH$_4$OH. The organic layer was separated, dried, filtered and the solvent evaporated. This fraction was purified by HPLC over silica gel (eluent: CH$_2$Cl$_2$/CH$_3$OH 97/3). A pure fraction was collected and the solvent was evaporated. The residue was crystallized from DIPE. The precipitate was filtered off and dried, yielding 15.7 g of 6,7,8,13-tetrahydro-5H-imidazo[2,1-b][3]benzazonine (18%) (interm. 20).

d) A mixture of DIPA (0.151 mol) in THF (650 ml) was stirred at −78° C. under N$_2$ flow. Butyllithium 2,5M in hexane (0.144 mol) was added dropwise at a temperature below −40° C. The mixture was stirred at −78° C. for 15 min. Intermediate (20) (0.072 mol) in a small amount of THF was added dropwise at a temperature below −55° C. The mixture was stirred at −78° C. for 1 hour. N,N-bis(2-chloroethyl)benzenemethanamine hydrochloride in a small amount of THF was added dropwise at a temperature below −50° C. The mixture was stirred at −78° C. for 1 hour, allowed to warm to room temperature overnight and decomposed with H$_2$O. The organic solvent was evaporated. The aqueous concentrate was extracted with CH$_2$Cl$_2$. The organic layer was separated, dried, filtered and the solvent was evaporated. This fraction was purified by column chromatography over silica gel (eluent: CH$_2$Cl$_2$/CH$_3$OH 100/0, 99/1, 98/2, 96/4, 94/6 and 92/8). A fraction was collected and the solvent was evaporated, yielding 5,6,7,8-tetrahydro-1'-(phenylmethyl)spiro[13H-imidazo[2,1-b][3]benzazonine-13,4'-piperidine] (interm. 21).

EXAMPLE A9

A mixture of 5,10-dihydro-imidazo[1,2-b]isoquinoline-7,8-diol, obtained according to the procedure described in Ex.No. A8c, (0.155 mol), phenyltrimethylammonium chloride (0.31 mol) and K$_2$CO$_3$ (0.68 mol) in DMF (400 ml) was stirred at 90° C. for 20 hours, cooled, poured out into H$_2$O and filtered over dicalite. The filtrate was separated into its layers. The organic layer was washed with H$_2$O, dried (MgSO$_4$), filtered and the solvent was evaporated. The residue was purified over silica gel on a glass filter (eluent: CH$_2$Cl$_2$/CH$_3$OH 100/0 to 97/3). The pure fractions were collected and the solvent was evaporated, yielding 3 g of 5,10-dihydro-7,8-dimethoxyimidazo[1,2-b]isoquinoline (8.4%) (interm. 22).

EXAMPLE A10

A mixture of intermediate (31) (see Table 1), prepared according to the procedure described in Ex.No. A8d, (0.01 mol) in HBr 48% solution (60 ml) was stirred and refluxed for 2 hours. The solvent was evaporated. The residue was taken up ina small amount of H$_2$O. The mixture was alkalized with K$_2$CO$_3$ and extracted with CH$_2$Cl$_2$/CH$_3$OH. The organic layer was separated, dried, filtered and the solvent was evaporated, yielding 4.3 g of 5,6-dihydro-1'-(phenylrnethyl)spiro[11H-imidazo-[2,1-b][3]benzazepine-11,4'-piperidine]-8,9-diol (100%) (interm. 23).

EXAMPLE A11

A mixture of compound (22) (0.0117 mol) and triethyl amine (0.0421 mol) in toluene (100 ml) was stirred and refluxed. Ethyl carbonochloridate (0.0702 mol) was added dropwise at reflux temperature. The mixture was stirred and refluxed for 1 hour, cooled, poured out into H$_2$O and K$_2$CO$_3$ (15 g) and separated into its layers. The aqueous layer was extracted with CH$_2$Cl$_2$. The combined organic layer was dried (MgSO$_4$), filtered and the solvent was evaporated. The residue was purified over silica gel on a glass filter (eluent: CH$_2$Cl$_2$/ethanol 96/4). The pure fractions were collected and the solvent was evaporated. The residue was boiled in DIPE. The precipitate was filtered off and dried, yielding 2.4 g of [1'-(ethoxycarbonyl)spiro[11H-imidazo[2,1-b]-[3]benzazepine-11,4'-piperidine)-6-yl]ethyl carbonate (33%) (interm. 24).

Table 1 lists intermediates which were prepared according to one of the above mentioned examples.

TABLE 1

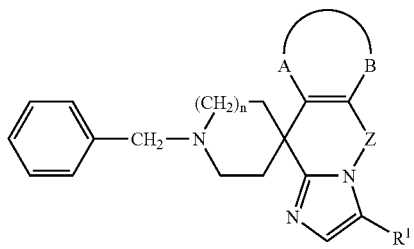

| Interm. No. | Ex. No. | n | z | R1 | —A—B— |
|---|---|---|---|---|---|
| 25 | A8d | 2 | —(CH$_2$)$_2$— | H | —CH=CH—CH=CH— |
| 3 | A2 | 1 | —CH$_2$— | H | —CH=CH—CH=CH— |
| 2 | A1b | 1 | —(CH$_2$)$_2$— | H | —CH=CH—CH=CH— |
| 26 | A8d | 1 | —(CH$_2$)$_2$— | H | —CH=CF—CH=CH— |
| 27 | A8d | 1 | —(CH$_2$)$_2$— | H | —CH=CH—CH=CCH$_3$— |
| 28 | A8d | 1 | —(CH$_2$)$_3$— | H | —CH=CH—CH=CH— |
| 29 | A8d | 1 | —(CH$_2$)$_2$— | H | —COH=CH—CH=CH— |
| 30 | A8d | 1 | —(CH$_2$)$_2$— | H | —CH=CH—COH=CH— |
| 31 | A8d | 1 | —(CH$_2$)$_2$— | H | —CH=COCH$_3$—COCH$_3$=CH— |
| 32 | A8d | 1 | —O—CH$_2$— | H | —CH=CH—CH=CH— |
| 23 | A10 | 1 | —(CH$_2$)$_2$— | H | —CH=COH—COH=CH— |
| 6 | A4a | 1 | —(CH$_2$)$_2$— | CH$_2$OH | —CH=CH—CH=CH— |
| 7 | A4b | 1 | —(CH$_2$)$_2$— | C(=O)H | —CH=CH—CH=CH— |
| 8 | A4c | 1 | —(CH$_2$)$_2$— | CH$_2$NH$_2$ | —CH=CH—CH=CH— |
| 10 | A5 | 1 | —(CH$_2$)$_2$— | CH$_2$NHC(=O)CH$_3$ | —CH=CH—CH=CH— |
| 9 | A4d | 1 | —(CH$_2$)$_2$— | CH$_2$NHC(=O)NH$_2$ | —CH=CH—CH=CH— |
| 5 | A3b | 1 | —(CH$_2$)$_2$— | C(=O)NH$_2$ | —CH=CH—CH=CH— |
| 21 | A8d | 1 | —(CH$_2$)$_4$— | H | —CH=CH—CH=CH— |
| 11 | A6 | 1 | —(CH$_2$)$_2$— | CH$_2$NHSO$_2$CH$_3$ | —CH=CH—CH=CH— |
| 33 | A8d | 1 | —(CH$_2$)— | H | —CH=COCH$_3$—COCH$_3$=CH— |

B. Preparation of Final Compounds

EXAMPLE B1

Preparative Example

A mixture of intermediate (2) (0.02 mol) in methanol (150 ml) was hydrogenated with palladium on charcoal 10% (2 g) as a catalyst at 50° C. for 18 hours. After uptake of H$_2$ (1 eq), the catalyst was filtered and the filtrate was evaporated, yielding 5,6-dihydrospiro[11H-imidazo[2,1-b][3]benzazepine-11,4'-piperidine] (comp. 6, not claimed). This fraction was converted into the hydrochloric acid salt (1:1) in CH$_3$CN, yielding 5 g of 5,6-dihydrospiro[imidazo[2,1-b][3]benzazepine-11[11H],4'-piperidine]monohydrochloride (86 can also be converted into the (E)-2-butenedioic acid salt.

EXAMPLE B2 a) A mixture of compound (6) (0.1 mol) and N,N-diethylethanamine (0.13 mol) in CH$_2$Cl$_2$ (300 ml) was stirred at a temperature below 10° C. Ethyl carbonochloridate (0.12 mol) was added dropwise at this temperature. The mixture was allowed to warm to room temperature and then stirred at room temperature for 1 hour. Water and K$_2$CO$_3$ (10 g) were added. The mixture was separated into its layers. The aqueous layer was extracted with CH$_2$Cl$_2$. The combined organic layer was dried (MgSO$_4$), filtered and the solvent was evaporated, yielding 35.4 g of ethyl 5,6dihydrospiro[11H-imidazo-[2,1-b][3]benzazepine-11,4'-piperidine]-1'-carboxylate (100%) (comp. 4).

b) A mixture of compound (4) (0.1 mol), sodium acetate (0.3 mol) and acetic acid (0.258 mol) in formaldehyde 38% solution (165 ml) was stirred and refluxed for 10 hours. The mixture was poured out into ice and a NaOH solution and extracted with CH$_2$Cl$_2$. The organic layer was separated, dried (MgSO$_4$), filtered and the solvent was evaporated. The residue was purified by column chromatography over silica gel (eluent: CH$_2$Cl$_2$/ethanol 95/5 to 90/10). The pure fractions were collected and the solvent was evaporated, yielding 16.5 g of ethyl 5,6-dihydro-3-(hydroxymethyl)spiro-[11H-imidazo[2,1-b][3]-benzazepine-11,4'-piperidine]-1'-carboxylate (46%) (comp. 5).

c) A mixture of compound (5) (0.046 mol) and potassium hydroxide (0.46 mol) in 2-propanol (130 ml) was stirred and refluxed for 7 hours. The solvent was evaporated. The residue was taken up in water and extracted with CH$_2$Cl$_2$. The organic layer was separated, dried (MgSO$_4$), filtered and the solvent was evaporated, yielding 11.5 g of 5,6-dihydrospiro[11H-imidazo[2,1-b][3]benzazepine-11,4'-piperidine]-3-methanol (88%) (comp. 18). Part of this fraction (1 g) was dissolved in CH$_3$OH and converted into the (E)-2-butenedioic acid salt (2:1). The precipitate was filtered off and dried, yielding 0.6 g of 5,6-dihydrospiro[11H-imidazo[2,1-b][3]benzazepine-11,4'-piperidine]-3-methanol (E)-2-butenedioic acid salt (2:1) (comp. 18a).

EXAMPLE B3

A mixture of compound (6) (0.01 mol) and (CH$_2$O)$_n$ (0.066 mol) in methanol (150 ml) and thiophene 4% solution (1 ml) was hydrogenated with palladium on charcoal 10% (1 g) as a catalyst at 50° C. After uptake of H$_2$ (1 eq), the catalyst was filtered and the filtrate was evaporated. The residue was taken up in H$_2$O/K$_2$CO$_3$/NH$_4$OH and stirred. The mixture was extracted with CH$_2$Cl$_2$, dried, filtered and evaporated. The residue was converted into the cyclohexanesulfamic acid salt (1:2) in 2-propanone and recrystallized twice from 2-propanol, yielding 2.44 g of 6,11-dihydro-1'-methylspiro[5H-imidazo[2,1-b][3]benzazepine-11,4'-piperidine]cyclohexylsulfamate (1:2) (40%) (comp. 1).

EXAMPLE B4 a) A mixture of 1-bromobutane (0.012 mol), compound (6) (0.01 mol), $Na_2CO_3$ (0.02 mol) and potassium iodide (few crystals) in 2-butanone (200 ml) was stirred and refluxed overnight. The mixture was evaporated, the residue was taken up in water and extracted with $CH_2Cl_2$. The organic layer was dried, filtered off and evaporated. The residue was purified by column chromatography over silica gel (eluent: $CH_2Cl_2$/($CH_3OH/NH_3$) 95/5). The pure fractions were collected and evaporated. The residue was converted into the hydrochloric acid salt (1:2) in 2-propanol. The precipitate was filtered and dried, yielding 0.7 g of 1'-butyl-5,6-dihydrospiro[imidazo[2,1-b][3]-benzazepine-11-[11H],4'-piperidine]dihydrochloride.hemihydrate (18%) (comp. 3).

b) A mixture of 1-(3-chloropropoxy)-4-fluorobenzene (0.018 mol), 5,6-dihydrospiro[11H-midazo[2,1-b][3]benzazepine-11,4'-piperidine] (0.015 mol), $Na_2CO_3$ (0.015 mol) and KI (10 mg) in 4-methyl-2-pentanone (200 ml) was stirred and refluxed for 18 hours. The mixture was poured into water, separated and the aqueous layer was extracted with $CH_2Cl_2$. The organic layer was dried (MgSO4), filtered off and evaporated. The residue was purified on a glass filter over silica gel (eluent: $CH_2Cl_2/CH_3OH$ 90/10). The pure fractions were collected and evaporated. The residue was converted into the cyclohexylsulfamic acid salt (1:2) in 2-propanone. Yielding: 4.26 g of 1'-[3-(4-fluorophenoxy)propyl]-5,6-dihydrospiro[imidazo[2,1-b][3]benzaepine-11-[11H],4'-piperidine]cyclohexylsulfamate (1:2) (37%); mp. 180° C. (comp. 71).

c) A mixture of 1-chloro-3-methyl-2-butene (0.02 mol), 5,6-dihydrospiro[11H-imidazo[2,1-b][3]benzazepine-11,4'-piperidine] (0.015 mol), $Na_2CO_3$ (0.015 mol) and KI (0.015 mol) in N,N-dimethylaceetamide (150 ml) was stirred at room temperature overnight. The mixture was filtered over dicalite and evaporated. The residue was taken up in $CH_2Cl_2$/water 95/5. The precipitate was filtered off and dried. Yielding: 0.86 g of 5,6-dihydro-1'-(3-methyl-2-butenyl)spiro[imidazo[2,1-b][3]benzazepine-11-[11H],4'-piperidine]monohydroiodide (12.7%); mp. 255.4° C. (comp. 74).

d) A mixture of 1-(2-bromoethyl)-4-ethyl-1,4-dihydro-5H-tetrazol-5-one (0.012 mol), 5,6-dihydrospiro[11H-imidazo[2,1-b][3]benzazepine-11,4'-piperidine] (0.01 mol), $Na_2CO_3$ (0.01 mol) and KI (10 mg) in 4-methyl-2-pentanone (200 ml) was stirred and refluxed for 18 hours. The mixture was poured into water. The mixture was separated and the aqueous layer was extracted with 3-methyl-2-butanone, dried (MgSO$_4$), filtered and evaporated. The residue was purified on a glass filter over silica gel (eluent: $CH_2Cl_2/CH_3OH$ 95/5 to 93/7). The pure fractions were collected and evaporated. The residue was converted into the hydrochloric acid salt (1:2) in $C_2H_5OH$. Yielding: 2.63 g of 1-[2-(5,6-dihydrospiro[11H-imidazo[2,1-b][3]benzazepin-11,4'-piperidin]-1'-yl)ethyl]-4-ethyl-1,4-dihydro-5H-tetrazol-5-one dihydrochloride (56%); mp. 230° C. (comp. 75).

e) A mixture of chloroacetonitrile (0.11 mol), 5,6-dihydrospiro[11H-imidazo[2,1-b]-[3]benzazepine-11,4'-piperidine] (0.1 mol) and N,N-diethylethanamine (0.12 mol) in DMF (400 ml) was stirred at room temperature for 48 hours. The mixture was poured into water and extracted with $CH_2Cl_2$. The organic layer was dried (MgSO$_4$), filtered off and evaporated. The residue was purified on a glass filter over silica gel (eluent: $CH_2Cl_2/CH_3OH$ 96/4). The pure fractions were collected and evaporated. The residue was crystallized from $CH_3CN$. Yielding: 18.5 g 5,6-dihydrospiro[imidazo[2,1-b][3]-benzazepine-11-[11H],4'-piperidine]-1'-acetonitrile (63%); mp. 152.6° C. (comp. 76).

EXAMPLE B5

Bis(1,1-dimethylethyl) dicarbonate (0.095 mol) dissolved in a small amount of $CH_2Cl_2$ was added dropwise to a stirring mixture of compound (6) (0.079 mol) in $CH_2Cl_2$ (250 ml). The mixture was stirred at room temperature for the weekend, then washed with $H_2O$, dried, filtered and the solvent was evaporated. Toluene was added and evaporated again. The residue was stirred in DIPE. The precipitate was filtered off and the filtrate was evaporated. This fraction was purified over silica gel on a glass filter (eluent: $CH_2Cl_2/CH_3OH$ 100/0, 99/1, 98/2 and 96/4). The pure fractions were collected and the solvent was evaporated. The residue was stirred in hexane. The precipitate was filtered off and dried, yielding 15.05 g of 1,1-dimethylethyl 5,6-dihydrospiro[11H-imidazo[2,1-b][3]benzazepine-11,4'-piperidine]-1'-carboxylate (54%) (comp. 7).

EXAMPLE B6 a) A mixture of tetrahydro-2-furanmethanol methanesulfonate (0.01 mol), compound 6 (0.01 mol) and $Na_2CO_3$ (0.02 mol) in 4-methyl-2-pentanone (150 m) was stirred and refluxed overnight. The reaction mixture was filtered over dicalite. The filtrate was evaporated. The residue was purified by column chromatography over silica gel (eluent: $CH_2Cl_2$/($CH_3OH/NH_3$) 95/5). The pure fractions were collected and the solvent was evaporated. The residue was dissolved in 2-propanone and converted into the cyclohexane sulfamic acid salt (1:2). The precipitate was filtered off and dried. Yielding: 1.48 g of 5,6-dihydro-1'-[(tetrahydro-2-furanyl)methyl]spiro[imidazo[2,1-b][3]benzazepine-11-[11H],4'-piperidine]cyclohexylsulfamate (1:2) monohydrate (20.7%); mp. 120.2° C. (comp. 72).

b) A mixture of compound 6 (0.02 mol) and 2-thiophenecarboxaldehyde (0.053 mol) in methanol (300 ml) was hydrogenated with Raney Nickel (2 g) as a catalyst. After uptake of $H_2$ (1 eq), the catalyst was filtered off and the filtrate was evaporated. The residue was purified by column chromatography over silica gel (eluent: $CH_2Cl_2/CH_3OH$ 95/5). The pure fractions were collected and evaporated. The residue was converted into the cyclohexanesulfamic acid salt (1:1) in 2-propanone. The precipitate was filtered off and dried. The residue was recrystallized from 2-propanol. The precipitate was filtered off and dried. Yielding: 0.72 g of 5,6-dihydro-1'-(2-thienylmethyl)spiro[imidazo[2,1-b][3]benzazepine-11-[11H],4'-piperidine]cyclohexylsulfamate (1:1) (6.6%); mp. 211.1° C. (comp. 73).

EXAMPLE B7 a) A mixture of compound (9) (0.155 mol), prepared according to the procedure described in Ex. No. B2 b, and $MnO_2$ (300 g) in chloroform (1200 ml) was stirred and refluxed for 90 min. The mixture was filtered over dicalite and the filtrate was evaporated. Part of this fraction (1 g) was crystallized from $CH_3CN$. The precipitate was filtered off and dried, yielding 0.5 g of 1,1-dimethylethyl 3-formyl-5,6-dihydrospiro[imidazo[2,1-b][3]benzazepine-11,4'-piperidine]-1'-carboxylate (comp. 12).

b) A mixture of compound (12) (0.134 mol), NaCN (0.705 mol) and $MnO_2$ (233 g) in methanol (2500 ml) was stirred at room temperature. Acetic acid (45.5 ml) was added dropwise. The mixture was stirred and refluxed for 20 hours and filtered over dicalite. The filtrate was evaporated. The residue was taken up in $H_2O$, $CH_2Cl_2$ and $K_2CO_3$. The mixture was separated into its layers. The aqueous layer was extracted with CH$_2$Cl$_2$. The combined organic layer was dried (MgSO$_4$), filtered and the solvent was evaporated. The residue was purified by column chromatography over silica gel (eluent: CH$_2$Cl$_2$/CH$_3$OH 97/3). A pure fraction was collected and the solvent was evaporated, yielding 47.7 g of methyl (1,1-dimethylethyl) 5,6-dihydrospiro[11H-imidazol[2,1-b][3]benzazepine-11,4'-piperidine]-3,1'-dicarboxylate (87%) (comp. 13).

c) A mixture of compound (13) (0.056 mol) in NaOH 1N (100 ml), H$_2$O (250 ml) and THF (250 ml) was stirred at room temperature for 18 hours. The organic solvent was evaporated. The aqueous concentrate was neutralized with HCl 1N (100 ml) and extracted with CH$_2$Cl$_2$. The organic layer was separated, dried (MgSO$_4$), filtered and the solvent was evaporated. Part of this fraction (2 g) was crystallized from CH$_3$CN. The precipitate was filtered off and dried, yielding 1.16 g of 1'-[(1,1-dimethylethoxy)-carbonyl]-5,6-dihydrospiro[11H-imidazo[2,1-b][3]benzazepine-11,4'-piperidine]-3-carboxylic acid (comp. 14).

d) A mixture of compound (14) (0.04 mol) and N,N-dimethyl-4-pyridinamine (0.04 mol) in CH$_2$Cl$_2$ (300 ml) was stirred until complete dissolution. N,N-diethylethanamine (0.05 mol) was added. Then N'-(ethylcarbonimidoyl)-N,N-dimethyl-1,3-propanediamine monohydrochloride (0.05 mol) was added portionwise. The mixture was stirred at room temperature for 30 min. N,N-diethylethanamine (0.06 mol) was added and then NH$_4$Cl (0.05 mol) was added portionwise. The mixture was stirred at room temperature overnight, poured out into H$_2$O and separated into its layers. The aqueous layer was extracted with CH$_2$Cl$_2$. The combined organic layer was dried (MgSO$_4$), filtered and the solvent was evaporated. The residue was purified by column chromatography over silica gel (eluent: CH$_2$Cl$_2$/CH$_3$OH 97.5/2.5). The pure fractions were collected and the solvent was evaporated. The residue was crystallized from CH$_3$CN. The precipitate was filtered off and dried, yielding 9.5 g of 1,1-dimethylethyl 3-(aminocarbonyl)-5,6-dihydrospiro[11H-imidazo[2,1-b][3]benzazepine-11,4'-piperidine]-1'-carboxylate (60%) (comp. 16).

e) A mixture of compound (16) (0.023 mol) in HCl/2-propanol (25 ml) and methanol (100 ml) was stirred and refluxed for 90 min and then cooled. The precipitate was filtered off and dried, yielding 8 g of 5,6-dihydrospiro[11H-imidazo[2,1-b][3]-benzazepine-11,4'-piperidine]-3-carboxamide dihydrochloride (94%) (comp. 17). The precipitate can also be converted into the (E)-2-butenedioic acid salt.

f) Preparation of compound 61

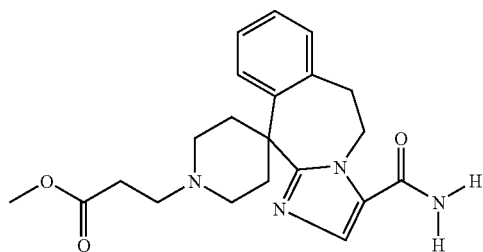

A mixture of compound (17) (0.0135 mol) and NaHCO$_3$ (0.0271 mol) in THF (100 ml) and ethanol (50 ml) was stirred and refluxed for 10 min. Methyl 2-propenoate (0.0149 mol) was added. The mixture was stirred and refluxed for 3 hours and then cooled. The solvent was evaporated under reduced pressure. The residue, was partitioned between H$_2$O and CH$_2$Cl$_2$. The organic layer was separated, dried (MgSO$_4$), filtered and the solvent evaporated. The residue was purified by column chromatography over silica gel (eluent: CH$_2$Cl$_2$/(CH$_3$OH/NH$_3$) 95/5 to 90/10). The pure fractions were collected and the solvent was evaporated. The residue was purified again by column chromatography over silica gel (eluent: CH$_2$Cl$_2$/(CH$_3$OH/NH$_3$) 99/1 to 97/3). The pure fractions were collected and the solvent was evaporated. The residue Was Refluxed in CH$_3$OH/diethyl ether 2:8 (precipitation resulted). The precipitate was filtered off, washed with diethyl ether and dried in vacuo at 40° C. overnight. Yielding: 2.27 g of compound 61.

g) N,N-diethylethanamine (0.0081 mol) was added at room temperature to a suspension of compound 17 (0.004 mol) in methanol (100 ml). The mixture was cooled to 0° C. Oxirane was bubbled through the mixture for 45 min. The mixture was allowed to warm to room temperature and then stirred at room temperature for 30 min. The solvent was evaporated under reduced pressure. The residue was purified by column chromatography over silica gel (eluent: CH$_2$Cl$_2$/(CH$_3$OH/NH$_3$) 97/3 to 95/5). The pure fractions were collected and the solvent was evaporated. The residue was crystallized from CH$_3$OH/CH$_2$Cl$_2$ 1:4. The precipitate was filtered off and dried. Yielding: 0.25 g of 6,11-dihydro-1'-(2-hydroxyetehyl)spiro[5H-imidazo[2,1-b][3]-benzazepine-11,4'-piperidine]-3-carboxamide (18%) (compound 62).

h) Preparation of compound 63

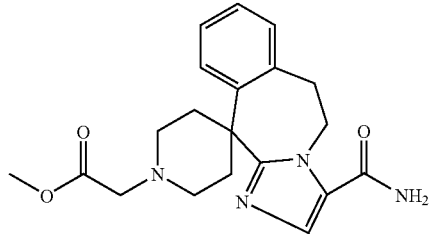

N,N-diethylethanamine (0.0113 mol) was added at room temperature to a suspension of compound 17 (0.0054 mol) in methanol (100 ml). After 5 min, oxirane was bubbled through the mixture at 0° C. for 1 hour. The solvent was evaporated. The residue was suspended in t-butanol (200 ml). Methyl chloroacetate (0.007 mol) and N,N-diethylethanamine (0.0054 mol) were added. The mixture was stirred and refluxed for 48 hours. The solvent was evaporated. The residue was purified by column chromatography over silica gel (eluent: CH$_2$Cl$_2$/(CH$_3$OH/NH$_3$) 98/2 to 95/5). Two fractions were collected and the solvent was evaporated. Fraction 1 was crystallized from CH$_3$OH/CH$_3$CN 1:3. The precipitate was filtered off and dried. The residue was purified by column chromatography over silica gel (eluent: CH$_2$Cl$_2$/(CH$_3$OH/NH$_3$) 97/3 to 95/5). The pure fractions were collected and the solvent was evaporated. Yielding: 0.46 g of compound 63.

i) N,N-diethylethanamine (0.0271 mol) was added at room temperature to a suspension of compound 17 (0.0129 mol) and ethyl α-methylenebenzeneacetate (0.0140 mol) in DMF (100 ml). The mixture was stirred at room temperature over the weekend. The solvent was evaporated. The residue was extracted with CH$_2$Cl$_2$/H$_2$O. The mixture was separated into its layers. The precipitate in the organic layer was filtered off. Yielding: 2.6 g of ethyl 3-(aminocarbonyl)-6,11-dihydro-α-phenylspiro[5H-imidazo-[2,1-b][3]benzazepine-11,4'-piperidine]-1'-propanoate monohydrochloride (compound 64).

j) Preparation of compound 65

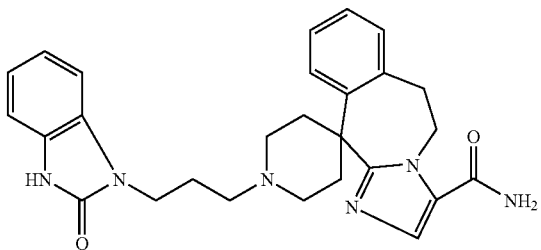

A mixture of compound 17 (0.0027 mol), 1-(3-chloropropyl)-1,3-dihydro-2H-benzimidazol-2-one (0.003 mol), Na$_2$CO$_3$ (0.0027 mol) and KI (few crystals) in CH$_3$CN (100 ml) was stirred and refluxed for 48 hours. The solvent was evaporated. The residue was purified by column chromatography over silica gel (eluent: CH$_2$Cl$_2$/(CH$_3$OH/NH$_3$) 99/1 to 95/5). Two fractions were collected and their solvents were evaporated. The desired fraction was purified again by column chromatography over silica gel (eluent: CH$_2$Cl$_2$/(CH$_3$OH/NH$_3$) 97/3 to 95/5). The pure fractions were collected and the solvent was evaporated. Yielding: 0.1 8 g of compound 65.

k) Preparation of compound 66

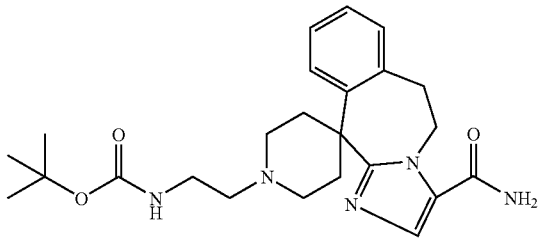

A mixture of isobutyl (2-chloroethyl)carbamoate (0.008 mol), 5,6-dihydrospiro[11H-imidazo[2,1-b][3]benzazepine-11,4'-piperidine]-3-carboxamide dihydrochloride (0.004 mol), 4-methyl-2-pentanone (50 ml), Na$_2$CO$_3$ (0.020 mol) and KI (catalytic quantity) was stirred and refluxed (oil bath: 130° C.) overnight. The solvent was evaporated (vacuum, 60° C.). Water was added. CH$_2$Cl$_2$/CH$_3$OH 90/10 was added. The organic layer was separated, dried (MgSO$_4$), filtered and the solvent was evaporated. The residue was purified by column chromatography over silica gel (eluent: CH$_2$Cl$_2$/(CH$_3$OH/NH$_3$) 95/5). The desired fractions were collected and the solvent was evaporated. Yield: 1.5 g of compound 66 (85.4%).

l) Preparation of compound 67

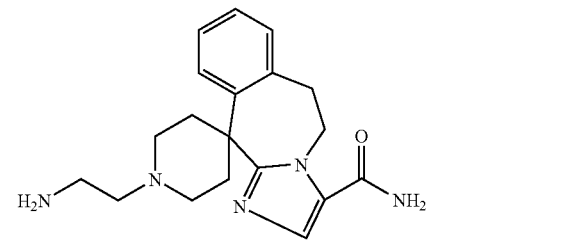

A mixture of compound 66 (0.00227 mol) and HCl/2-propanol (3 ml) in 2-propanol (30 ml) was stirred at 80° C. (oil bath). The solvent was evaporated (vacuum, 40° C.). 2-Propanol was added, then evaporated (2×). Ethanol was added, then evaporated. The residue was stirred in boiling ethanol (50 ml), then filtered off over a P4 glass filter and the product was dried under a stream of N$_2$. Yield: 0.254 g (24.0%). The filtrate was stirred for 3 hours while cooling on an ice-bath. The precipitate was filtered off over a P3 glass filter and dried (vacuum, 60° C., 3 hours). Yield: 0.304 g (28.7%). The filtrate was evaporated. The residue was dried (over the weekend under N$_2$ flow). Total yield: 70.4% of compound 67.

m) Methyl chloroformate (0.0036 mol) was added at room temperature to a suspension of compound (17) (0.0032 mol) in CH$_2$Cl$_2$ (100 ml). A mixture of N,N-diethylethanamine (0.0097 mol) in CH$_2$Cl$_2$ (20 ml) was added dropwise. The mixture was stirred at room temperature for the weekend. The solvent was evaporated. The residue was purified by column chromatography over silica gel (eluent: CH$_2$Cl$_2$/CH$_3$OH 99/1 to 98/2). The pure fractions were collected and the solvent was evaporated. The residue was crystallized from CH$_3$CN. The precipitate was filtered off and dried. Yield: 0.68 g of 3-(aminocarbonyl)-6,11-dihydrospiro[5H-imidazo[2,1-b][3]-benzazepine-11,4'-piperidine]-1'-carboxylate (60%) (comp. 79).

n) A mixture of compound (17) (0.005 mol), KOAc (2 g) and paraformaldehyd (0.5 g) in methanol (100 ml) was hydrogenated with palladium on charcoal 10% (0.5 g) as a catalyst in the presence of a thiophene solution (1 ml). After uptake of H$_2$ (1 equiv), the catalyst was filtered off and the filtrate was evaporated. The residue was purified by column chromatography over silica gel (eluent: CH$_2$C$_2$/(CH$_3$OH/NH$_3$) 97/3). The pure fractions were collected and the solvent was evaporated. This fraction was purified again by column chromatography over silica gel (eluent: CH$_2$Cl$_2$/(CH$_3$OH/NH$_3$) 97/3 to 95/5). The pure fractions were collected and the solvent was evaporated. Yield: 0.43 g of 6,11-dihydro-1'-methylspiro[5H-imidazo[2,1-b][3] benzazepine-11,4'-piperidine]-3-carboxamide monohydrate (28%) (comp. 80).

EXAMPLE B8 a) A solution of compound (7) (1.63 mol) in CH$_2$Cl$_2$ (7500 ml) was cooled to 0° C. under N$_2$ flow. 1-Bromo-2,5-pyrrolidinedione (1.63 mol) was added portionwise (29 g each). H$_2$O (3000 ml) was added. The mixture was stirred overnight. The organic layer was separated, dried, filtered and the solvent was evaporated. This fraction was purified by HPLC over silica gel (eluent: CH$_2$Cl$_2$/CH$_3$OH 100/0, 98/2, 90/10 and 100/0). A pure fraction was collected and the solvent was evaporated, yielding 189 g of 1,1-dimethylethyl 2,3-dibromo-5,6-dihydrospiro[11H-imidazo[2,1-b][3] benzazepine-11,4'-piperidine]-1'-carboxylate (27%) (comp. 48). The 3-monobromo analogue (comp. 60; Ex. No. B10a) can be prepared in a similar way.

b) A mixture of compound (48) (0.02 mol), acetic acid, palladium(2+) salt (0.15 g) and 1,3-propanediylbis [diphenylphosphine] (0.55 g) in TBF (150 ml) was stirred in an autoclave at 150° C. for 16 hours under pressure of CO gas (30 bar) and NH$_3$ gas (10 atm). The mixture was cooled, filtered and the filtrate was evaporated. This fraction was purified over silica gel on a glass filter (eluent: CH$_2$Cl$_2$/CH$_3$OH 95/5). The pure fractions were collected and the solvent was evaporated. The residue was crystallized from CH$_3$CN. The precipitate was filtered off and dried, yielding 1,1-dimethylethyl 2,3-bis(aminocarbonyl)-5,6-dihydrospiro [11H-imidazo[2,1-b][3]benzazepine-11,4'-piperidine]-1'-carboxylate (comp. 49).

EXAMPLE B9

Dibenzoyl peroxide (0.5 g) was added to a stirring mixture of compound (7) (0.039 mol) in CH$_2$Cl$_2$ (210 ml). 1-Chloro-2,5-pyrrolidinedione (0.078 mol) in a small amount of CH$_2$Cl$_2$ was added dropwise. The mixture was stirred at room temperature overnight. The solvent was evaporated. H$_2$O was added and the mixture was extracted with CH$_2$Cl$_2$. The organic layer was separated, dried, filtered and the solvent was evaporated. The residue was purified over silica gel on a glass filter (eluent: CH$_2$Cl$_2$/CH$_3$OH 100/0, 99/1, 9812, 96/4 and 94/6). The pure fractions were collected and the solvent was evaporated. Some starting material (7.5 g; 0.02 mol) was recuperated. The reaction was carried out again. Dibenzoyl peroxide (0.5 g) was added to a stirring mixture of compound (7) (0.02 mol) in CH$_2$Cl$_2$ (210 ml). 1-Chloro-2,5-pyrrolidinedione (0.078 mol) in a small amount of CH$_2$Cl$_2$ was added dropwise. The mixture was stirred at room temperature overnight. The solvent was evaporated. H$_2$O was added and the mixture was extracted with CH$_2$Cl$_2$. The organic layer was separated, dried, filtered and the solvent was evaporated. The residue was purified over silica gel on a glass filter (eluent: CH$_2$Cl$_2$/CH$_3$OH 100/0, 99/1 and 98.5/1.5). The pure fractions were collected and the solvent was evaporated. The residue was combined with the one obtained from the first reaction, yielding 14 g of 1,1-dimethylethyl 3-chloro-5,6-dihydrospiro[11H-imidazo[2,1-b[]3]benzazepine-11,4'-piperidine]-1'-carboxylate (93%) (comp. 19).

EXAMPLE B10 a) CH$_2$Cl$_2$ (87 ml) was added to 1,1-dimethylethyl 5,6-dihydrospiro[11H-imidazo[2,1-b][3]benzazepine-11,4'-piperidine]-1'-carboxylate (comp. 7) in methanol (0.0582 mol). Water (58 ml) was added. Water (58 ml) and Na$_2$CO$_3$ (0.0582 mol) were added to the separated organic layer and the mixture was cooled to 0–5° C. (solution 1).

Br$_2$ (0.0565 mol) was added to a solution of tetrabutylammoniumbromide (0.0565 mol) and CH$_2$Cl$_2$ (29 ml). This mixture was stirred for 25 minutes at 15–25° C. and added to solution 1 during 1 hour. After stirring for 1 hour at 20° C., water (58 ml) was added. The separated organic layer was evaporated. 3-Methyl-2-butanone (87 ml) and water (29 ml) were added to the oily residue and this mixture was heated to 80° C. The separated organic layer was wased with water (29 ml) at 80° C. The organic layer was azeotroped till 116° C. 3-Methyl-2-butanone (40.7 ml) was distilled off and the product was crystallized during 2 hours at 50° C. The crystallized product was filtered off, washed with 3-methyl-2-butanone and dried (vacuum, 50° C.). Yield: 13.03 g of 1,1-dimethylethyl 3-bromo-5,6-dihydrospiro[11H-imidazo[2,1-b][3]benzazepine-11,4'-piperidine]-1'-carboxylate (51.8%) (comp. 60).

b) A mixture of compound (60) (0.257 mol), DMF (515 ml), H$_2$O (26 ml) and CuC.N (1,287 mol) were heated till 132° C., stirred for 17 hours and then cooled to room temperature. The mixture was poured into 2056 ml of H$_2$O and stirred for 2 hours. The precipitate was filtered off, washed twice with H$_2$O (149 ml) and dried (vacuum, 100° C.). The resulting precipitate was refluxed in 3-methyl-2-butanone (772 ml) for 30 min, followed by cooling the reaction mixture to 50° C. and filtering. NH$_4$OH (129 ml) was added to the filtrate at 50° C. and stirred for 30 min. The 3-methyl-2-butanone layer was separated and washed with NH$_4$OH (129 ml) as described above. This procedure was repeated for another 5 times. The 3-methyl-2-butanone layer was separated again, azeotroped for 30 min and partially evaporated. The resulting mixture was crystallized and the precipitate was filtered, washed with 3-methyl-2-butanone (7.7 ml) and dried (vacuum, 50° C.). Yield: 52.4 g of 1,1-dimethylethyl 3-(aminocarbonyl)-5,6-dihydrospiro[11H-imidazo[2,1-b][3]benzazepine-11,4'-piperidine]-1'-carboxylate (53%) (comp. 16).

EXAMPLE B11 a) A mixture of intermediate (18) (0.152 mol) in trifluoromethanesulfonic acid (500 ml) was stirred at 158° C. for 90 hours. The mixture was cooled, poured out on ice and K$_2$CO$_3$ (800 g) and extracted with CH$_2$Cl$_2$. The organic layer was separated, dried (MgSO$_4$), filtered and the solvent was evaporated partially until 100 ml while the temperature was kept below 40° C. The concentrate was purified immediately by column chromatography over silica gel (eluent: CH$_2$Cl$_2$/(CH$_3$OH/NH$_3$) 95/5). The pure fractions were collected and the solvent was evaporated, yielding 18.1 g of 1-methylspiro[11H-imidazo[2,1-b][3]benzazepine-11,4'-piperidin]-6(5H)-one (42%) (comp. 22). Part of this fraction (1.5 g) was dissolved in ethanol and converted into the (E)-2-butenedioic acid salt (2:3). The precipitate was filtered off and dried, yielding 1.92 g of 1-methylspiro[11H-imidazo[2,1-b][3]benzazepine-11,4'-piperidin]-6(5H)-one (E)-2-butenedioic acid salt (2:3) (comp. 22a).

b) A mixture of intermediate (24) (0.041 mol) in HBr 48% solution (250 ml) was stirred and refluxed for 4 hours. The mixture was poured out on ice and K$_2$CO$_3$ and extracted with CH$_2$Cl$_2$. The organic layer was separated, dried (MgSO$_4$), filtered and the solvent was evaporated, yielding 10.4 g of spiro[11H-imidazo[2,1-b][3]benzazepine-11,4'-piperidin]-6(5H)-one (95%) (comp. 23). Part of this fraction (0.9 g) was dissolved in ethanol and converted into the (E)-2-butenedioic acid salt (2:3). The precipitate was filtered off and dried, yielding 0.78 g of spiro[11H-imidazo[2,1-b][3]benzazepine-11,4'-piperidin]-6(5H)-one (E)-2-butenedioic acid salt (2:3) (comp. 23a).

c) A mixture of compound (23) (0.01 mol) in methanol (300 ml) was stirred on an ice bath. NaBH$_4$ (0.02 mol) was added portionwise over a 15-min period. The mixture was stirred on an ice bath for 1 hour. The solvent was evaporated at a temperature below 40° C. The residue was taken up in H$_2$O and the mixture was extracted with CH$_2$Cl$_2$/CH$_3$OH 90/10. The organic layer was separated, dried (MgSO$_4$), filtered and the solvent was evaporated, yielding 2 g of 5,6-dihydrospiro[11H-imidazo[2,1-b][3]-benzazepine-11,4'-piperidine]-6-ol (75%) (comp. 26).

d) A mixture of compound (26) (0.0075 mol) in methanesulfonic acid (50 ml) was stirred at room temperature for 40 min. The mixture was poured out on ice, alkalized with a NaOH 50% solution and extracted with CH$_2$Cl$_2$. The organic layer was separated, dried (MgSO$_4$), filtered and the solvent was evaporated, yielding 2 g of spiro[11H-imidazo[2,1-b][3]benzazepine-11,4'-piperidine] (100%) (comp.27). Part of this fraction (0.3 g) was dissolved in ethanol and converted into the (E)-2-butenedioic acid salt (1:1). The precipitate was filtered off and dried, yielding 0.26 g spiro[11H-imidazo[2,1-b][3]benzazepine-11,4'-piperidine] (E)-2-butenedioic acid salt (1:1) (comp. 27a).

EXAMPLE B12

A mixture of compound (24) (0.0128 mol) in H$_2$SO$_4$ (5 ml) and methanol (100 ml) was stirred and refluxed for the weekend. The solvent was evaporated. The residue was taken up in H$_2$O. The mixture was alkalized with a NaOH solution and extracted with CH$_2$Cl$_2$. The organic layer was separated, dried, filtered and the solvent was evaporated, yielding 4.4 g of 5,6-dihydro-2,3-bis(methoxymethyl)spiro[11H-imidazo-[2,1-b][3]benzazepine-11,4'-piperidine] (100%) (comp. 31).

EXAMPLE B13 a) A mixture of 5,6-dihydrospiro[imidazo[2,1-b][3]benzazepine-11-[11H],4'-piperidine)-1'-acetonitrile (comp.

76) (0.055 mol) in NH₃/CH₃OH (500 ml) was hydrogenated with Raney Nickel (2 g) as a catalyst at room temperature. After uptake of H₂ (2 eq), the catalyst was filtered off and the filtrate was evaporated. Yielding: 20.9 g of 5,6-dihydrospiro[imidazo[2,1-b][3]benzazepine-11-[1 H],4'-piperidine]-1'-ethanamine 2-propanolate (2:1). trihydrochloride. sesquihydrate; mp. 245.9° C. (comp. 77).

b) A mixture of 2-chloropyrimidine (0.012mol), 5,6-dihydrospiro[imidazo[2,1-b][3]-benzazepine-11-[11H],4'-piperidine]-1'-ethanamine (0.01 mol) and Na₂CO₃ (0.02mol) in 4-methyl-2-pentanone (200 ml) was stirred and refluxed for 48 hours. The reaction mixture was filtered over dicalite. The filtrate was evaporated. The residue was purified by column chromatography over silica gel (eluent: CH₂Cl₂/(CH₃OH/NH₃) 95/5). The pure fractions were collected and the solvent was evaporated. The residue was dissolved in 2-propanol and converted into the hydrochloric acid salt (1:3). The precipitate was filtered off and dried. Yielding: 0.94 g of 5,6-dihydro-N-2-pyrirnidinyl-spiro[imidazo[2,1-b][3]benzazepine-11-[11H],4'-piperidine]-1'-ethanamine trihydrochloride. monohydrate.2-propanolate (1:1) (16.7%) (comp. 78).

c) 3-Chloro-6-(3-methyl-1,2,4-thiadiazol-5-yl)pyridazine (0.01 mol) and 5,6-dihydrospiro[imidazo[2,1-b][3]benzazepine-11-[11H],4'-piperidine]-1'-ethanamine (0.01 were stirred at 140° C. for 2 h. The mixture was cooled and purified by column choromatography over silica gel (eluent: CH₂Cl₂/(CH₃OH/NH₃) 95/5). The pure fractions were collected and evaporated. The residue was converted into the hydrochloric acid salt (1:4) in 2-propanol and dried. Yielding: 2.22 g of 2-[[2-(5,6-dihydrospiro[imidazo[2,1-b][3]benzazepine-11-[11H],4'-piperidin-1'-yl)ethyl]amino]4(1H)-pyrimidinone trihydrochloride.2-propanolate (1:1). sesquihydrate (36.6%) (comp. 68).

The following Tables list compounds of formula (I) as prepared according to one of the above examples (Ex. No.).

TABLE 2

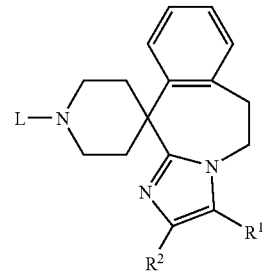

| Co. No. | Ex. No. | R₁ | R₂ | L | Salt/Melting point |
|---|---|---|---|---|---|
| 1 | B3 | H | H | CH₃ | (1); mp. 182.8° C. |
| 3 | B4a | H | H | CH₂CH₂CH₂CH₃ | mp. 268.5° C. |
| 4 | B2a | H | H | C(=O)OCH₂CH₃ | — |
| 5 | B2b | CH₂OH | H | C(=O)OCH₂CH₃ | — |
| 6 | B1 | H | H | H | — |
| 6a | B1 | H | H | H | (2); mp. 278.5° C. |
| 7 | B5 | H | H | C(=O)OC(CH₃)₃ | — |
| 9 | B2b | CH₂OH | H | C(=O)OC(CH₃)₃ | — |
| 10 | B2b | CH₂OH | CH₂OH | C(=O)OC(CH₃)₃ | — |
| 12 | B7a | C(=O)H | H | C(=O)OC(CH₃)₃ | — |
| 13 | B7b | C(=O)OCH₃ | H | C(=O)OC(CH₃)₃ | — |
| 14 | B7c | C(=O)OH | H | C(=O)OC(CH₃)₃ | — |
| 15 | B7e | C(=O)OCH₃ | H | H | — |
| 15a | B7e | C(=O)OCH₃ | H | H | (3); — |
| 18 | B2c/B7e | CH₂OH | H | H | — |
| 18a | B2c | CH₂OH | H | H | (4); — |
| 19 | B9 | Cl | H | C(=O)OC(CH₃)₃ | — |
| 20 | B7e | Cl | H | H | (3); — |
| 24 | B7e | CH₂OH | CH₂OH | H | — |
| 31 | B12 | CH₂OCH₃ | CH₂OCH₃ | H | — |
| 35 | B1 | CH₂NHC(=O)CH₃ | H | H | — |
| 39 | B1 | CH₂NHC(=O)NH₂ | H | H | — |
| 43 | B1 | CH₂NHSO₂CH₃ | H | H | — |
| 48 | B8a | Br | Br | C(=O)OC(CH₃)₃ | — |
| 49 | B8b | C(=O)NH₂ | C(=O)NH₂ | C(=O)OC(CH₃)₃ | — |
| 51 | B7e | CH₂OCH₃ | CH₂OH | H | — |
| 52 | B7e | CH₂OH | CH₂OCH₃ | H | — |
| 53 | B7e | C(=O)NH₂ | C(=O)NH₂ | H | (2); — |

(1) cyclohexylsulfamate (1:2);
(2) hydrochloric acid (1:2);
(3) (E)-2-butenedioate (1:1);
(4) (E)-2-butenedioate (2:1)

TABLE 3

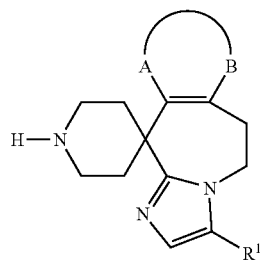

| Co No. | Ex. No. | R₁ | —A—B— | Salt/Melting point |
|---|---|---|---|---|
| 8 | B1 | H | —CH=CF—CH=CH— | (5); — |
| 11 | B1 | H | —CH=CH—CH=CCH₃— | |
| 21 | B1 | H | —CH=C(OH)—CH=CH— | — |
| 29 | B1 | H | —C(OH)=CH—CH=CH— | — |
| 30 | B1 | H | —CH=CH—C(OH)=CH— | — |
| 32 | B1 | H | —CH=C(OCH₃)—C(OCH₃)=CH— | — |
| 32a | B1 | H | —CH=C(OCH₃)—C(OCH₃)=CH— | (6); — |
| 34 | B1 | H | —CH=C(OH)—C(OH)=CH— | — |
| 46 | B7e | CH₂OH | —CH=C(OCH₃)—C(OCH₃)=CH— | — |
| 50 | B7e | Cl | —CH=C(OCH₃)—C(OCH₃)=CH— | — |
| 54 | B2c | H | —CH=CH—S— | — |
| 55 | B1 | H | —CH=CH—N(CH₃)— | — |
| 57 | B2c | H | —S—CH=CH— | — |
| 58 | B12 | —CH₂—O—CH₃ | —CH=CH—CH=CH— | — |

(3) (E)-2-butenedioate (1:1);
(5) hydrochloric acid (1:1);
(6) (E)-2-butenedioate (2:3)

TABLE 4

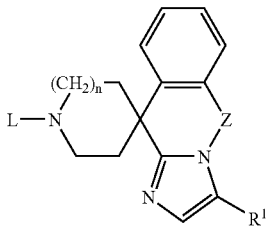

| Co. No. | Ex. No. | n | z | R₁ | L | Salt/Melting point |
|---|---|---|---|---|---|---|
| 2 | B1 | 2 | —(CH₂)₂— | H | H | (5); mp. 238.6° C. |
| 22 | B11a | 1 | —C(=O)CH₂— | H | CH₃ | — |
| 22a | B11a | 1 | —C(=O)CH₂— | H | CH₃ | (6); — |
| 23 | B11b | 1 | —C(=O)CH₂— | H | H | — |
| 23a | B11b | 1 | —C(=O)CH₂— | H | H | (6); — |
| 25 | B1 | 1 | —CH₂— | H | H | — |
| 25a | B1 | 1 | —CH₂— | H | H | (3); — |
| 26 | B11c | 1 | —CHOH—CH₂— | H | H | — |
| 27 | B11d | 1 | —CH=CH— | H | H | — |
| 27a | B11d | 1 | —CH=CH— | H | H | (3); — |
| 28 | B1 | 1 | —(CH₂)₃— | H | H | — |
| 33 | B1 | 1 | —O—CH₂— | H | H | — |
| 33a | B1 | 1 | —O—CH₂— | H | H | (3); — |
| 36 | B5 | 1 | —(CH₂)₃— | H | C(=O)OC(CH₃)₃ | — |
| 37 | B2b | 1 | —(CH₂)₃— | CH₂OH | C(=O)OC(CH₃)₃ | — |
| 38 | B7e | 1 | —(CH₂)₃— | CH₂OH | H | — |
| 42 | B1 | 1 | —(CH₂)₄— | H | H | — |
| 59 | B3 | 2 | —(CH₂)₂— | H | CH₃ | mp. 119.2° C. |
| 60 | B10a | 1 | —(CH₂)₂— | Br | —C(=O)OC(CH₃)₃ | — |

(3) (E)-2-butenedioate (1:1);
(5) hydrochloric acid (1:1);
(6) (E)-2-butenedioate (2:3)

TABLE 5

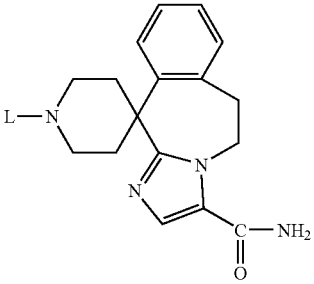

| Co. No. | Ex. No. | L | Salt/Melting point |
|---|---|---|---|
| 61 | B7f | —(CH$_2$)$_2$—C(=O)OCH$_3$ | (7) |
| 62 | B7g | —(CH$_2$)$_2$—OH | — |
| 63 | B7h | —CH$_2$—C(=O)OCH$_3$ | — |
| 64 | B7i | 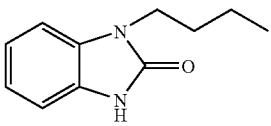 | (5) |
| 65 | B7j | 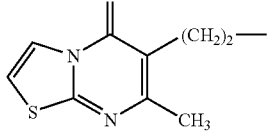 | (7) |
| 66 | B7k | —(CH$_2$)$_2$—NH—C(=O)OC(CH$_3$)$_3$ | — |
| 67 | B7l | —(CH$_2$)$_2$—NH$_2$ | (8) |
| 16 | B7d/B10b | —C(=O)OC(CH$_3$)$_3$ | — |
| 17 | B7e | H | (2); mp. 275.6° C. |
| 41 | B1 | H | — |
| 79 | B7m | —C(=O)OCH$_3$ | — |
| 80 | B7n | —CH$_3$ | (7); — |

(2) hydrochloric acid (1:2);
(5) hydrochloric acid (1:1);
(7) monohydrate;
(8) hydrochloric acid (1:3) monohydrate

TABLE 6

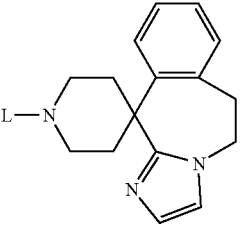

| Co. No. | Ex. No. | L | Salt/Melting point |
|---|---|---|---|
| 69 | B4d | 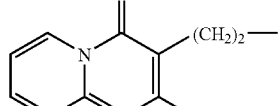 | (9); mp. 260.4° C.; |
| 70 | B4d | 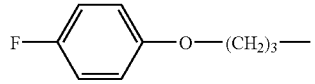 | mp. 189.0° C. |
| 71 | B4b | 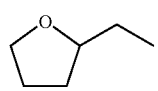 | (1); mp. 180° C.; |
| 72 | B6a | 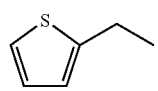 | (10); mp. 120.2° C.; |
| 73 | B6b | 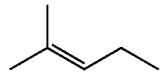 | (11); mp. 211.1° C. |
| 74 | B4c | 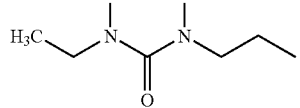 | (12); mp. 255.4° C. |
| 75 | B4d | 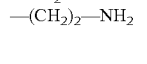 | (2); mp. 230° C. |
| 76 | B4e | —CH$_2$—CN | mp. 152.6° C. |
| 77 | B13a | —(CH$_2$)$_2$—NH$_2$ | (13); mp. 245.9° C. |
| 78 | B13b | 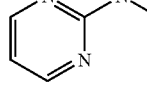 | (14); mp. 216.1° C. |
| 68 | B13c | 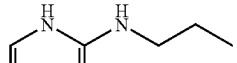 | (15); mp. 261.3° C. |

(1) cyclohexylsulfamate (1:2);
(2) hydrochloric acid (1:2);
(9) hydrochloric acid (1:3) hydrate (2:1) ethanolate (2:1);
(10) cyclohexylsulfamate (1:2) hydrate (1:2);
(11) cyclohexylsulfamate (1:1);
(12) hydroiodic acid (1:1);
(13) hydrochloric acid (1:3) hydrate (2:3) 2-propanolate (2:1);
(14) hydrochloric acid (1:3) hydrate (1:1) 2-propanolate (1:1);
(15) hydrochloric acid (1:3) hydrate (2:3) 2-propanolate (1:1)

TABLE 7

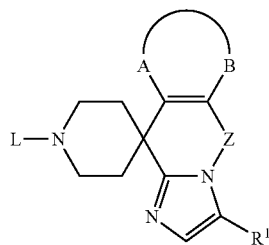

| Co. No. | Ex. No. | z | R₁ | —A—B— | L | Salt |
|---|---|---|---|---|---|---|
| 40 | B5 | —(CH$_2$)$_2$— | H | —CH=C(OCH$_3$)—C(OCH$_3$)=CH— | C(=O)OC(CH$_3$)$_3$ | — |
| 44 | B9 | —(CH$_2$)$_2$— | Cl | —CH=C(OCH$_3$)—C(OCH$_3$)=CH— | C(=O)OC(CH$_3$)$_3$ | — |
| 44a | B7e | —(CH$_2$)$_2$— | Cl | —CH=C(OCH$_3$)—C(OCH$_3$)=CH— | C(=O)OC(CH$_3$)$_3$ | (3); — |
| 45 | B2b | —(CH$_2$)$_2$— | CH$_2$OH | —CH=C(OCH$_3$)—C(OCH$_3$)=CH— | C(=O)OC(CH$_3$)$_3$ | — |
| 47 | B1 | —CH$_2$— | H | —CH=C(OCH$_3$)—C(OCH$_3$)=CH— | H | — |
| 47a | B1 | —CH$_2$— | H | —CH=C(OCH$_3$)—C(OCH$_3$)=CH— | H | (3); — |
| 56 | B2c | —CH=CH— | H | —CH=CH—S— | H | — |
| 56a | B2c | —CH=CH— | H | —CH=CH—S— | H | (3) |

(3) (E)-2-butenedioate (1:1)

C. Pharmacological Example

The ED$_{50}$ values (mg/kg) in the test "Protection of Rats from Compound 48/80 induced Lethality" for the compounds of formula (I) are listed in the Table below.

| Compound No. | ED$_{50}$ (mg/kg) |
|---|---|
| 1 | 2.5 |
| 3 | 2.5 |
| 17 | 0.04 |
| 18a | 0.08 |
| 20 | 0.31 |
| 53 | 0.31 |
| 56a | 2.5 |
| 58 | 2.5 |
| 62 | 0.63 |
| 64 | 0.31 |
| 79 | 0.04 |
| 80 | 0.63 |

D. Composition Examples

The following formulations exemplify typical pharmaceutical compositions suitable for systemic or topical administration to warm-blooded animals in accordance with the present invention.

"Active ingredient" (A.I.) as used throughout these examples relates to a compound of formula (I), a prodrug, an addition salt, a N-oxide, a quaternary amine or a stereochemically isomeric form thereof.

EXAMPLE D1

Oral Drops 500 g of the A.I. is dissolved in 0.5 l of 2-hydroxypropanoic acid and 1.5 l of the polyethylene glycol at 60~80° C. After cooling to 30~40° C. there are added 35 l of polyethylene glycol and the mixture is stirred well. Then there is added a solution of 1750 g of sodium saccharin in 2.5 l of purified water and while stirring there are added 2.5 l of cocoa flavor and polyethylene glycol q.s. to a volume of 50 l, providing an oral drop solution comprising 10 mg/ml of the A.I. The resulting solution is filled into suitable containers.

EXAMPLE D2

Oral Solutions 9 g of methyl 4-hydroxybenzoate and 1 g of propyl 4-hydroxybenzoate are dissolved in 4 l of boiling purified water. In 3 l of this solution are dissolved first 10 g of 2,3-dihydroxybutanedioic acid and thereafter 20 g of the A.I. The latter solution is combined with the remaining part of the former solution and 12 l of 1,2,3-propanetriol and 3 l of sorbitol 70% solution are added thereto. 40 g of sodium saccharin are dissolved in 0.5 l of water and 2 ml of raspberry and 2 ml of gooseberry essence are added. The latter solution is combined with the former, water is added q.s. to a volume of 20 l providing an oral solution comprising 5 mg of the A.I. per teaspoonful (5 ml). The resulting solution is filled in suitable containers.

EXAMPLE D3

Capsules 20 g of the A.I., 6 g sodium lauryl sulfate, 56 g starch, 56 g lactose, 0.8 g colloidal silicon dioxide, and 1.2 g magnesium stearate are vigorously stirred together. The resulting mixture is subsequently filled into 1000 suitable hardened gelatin capsules, each comprising 20 mg of the A.I.

EXAMPLE D4

Film-coated Tablets

Preparation of Tablet Core

A mixture of 100 g of the A.I., 570 g lactose and 200 g starch is mixed well and thereafter humidified with a solution of 5 g sodium dodecyl sulfate and 10 g polyvinylpyrrolidone (Kollidon-K 90®) in about 200 ml of water. The wet powder mixture is sieved, dried and sieved again. Then there are added 100 g microcrystalline cellulose (Avicel®) and 15 g hydrogenated vegetable oil (Sterotex ®). The whole is mixed well and compressed into tablets, giving 10,000 tablets, each comprising 10 mg of the active ingredient.

Coating

To a solution of 10 g methyl cellulose (Methocel 60 HG®) in 75 ml of denaturated ethanol there is added a solution of 5 g of ethyl cellulose (Ethocel 22 cps ®) in 150 ml of dichloromethane. Then there are added 75 ml of dichloromethane and 2.5 ml 1,2,3-propanetriol. 10 g of polyethylene glycol is molten and dissolved in 75 ml of dichloromethane. The latter solution is added to the former and then there are added 2.5 g of magnesium octadecanoate, 5 g of polyvinylpyrrolidone and 30 ml of concentrated colour suspension (Opaspray K-1-2109®) and the whole is homogenated. The tablet cores are coated with the thus obtained mixture in a coating apparatus.

What is claimed is:

1. A compound of formula

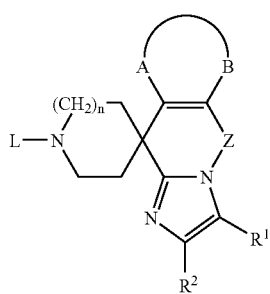

(I)

or a N-oxide, an addition salt, a quaternary amine or a stereochemically isomeric form thereof wherein $R^1$ is hydrogen, $C_{1-6}$alkyl, halo, formyl, carboxyl, $C_{1-6}$alkyloxycarbonyl, $C_{1-6}$alkylcarbonyl, $N(R^3R^4)C(=O)—$, $N(R^3R^4)C(=O)N(R^5)—$, ethenyl substituted with carboxyl or $C_{1-6}$alkyloxycarbonyl, or $C_{1-6}$alkyl substituted with hydroxy, carboxyl, $C_{1-6}$alkyloxy, $C_{1-6}$alkyloxycarbonyl, $N(R^3R^4)C(=O)—$, $C_{1-6}$alkylC(=O)N(R^5)—$, $C_{1-6}$alkylS(=O)_2N(R^5)—$ or $N(R^3R^4)C(=O)N(R^5)—$;

wherein each $R^3$ and each $R^4$ independently are hydrogen or $C_{1-4}$alkyl;

$R^5$ is hydrogen or hydroxy;

$R^2$ is hydrogen, $C_{1-6}$alkyl, hydroxy$C_{1-6}$alkyl, $C_{1-6}$alkyloxy$C_{1-6}$alkyl, $N(R^3R^4)C(=O)—$, aryl or halo;

n is 1 or 2;

—A—B— represents a bivalent radical of formula

—Y—CH=CH— (a-1);

—CH=CH—Y— (a-2); or

—CH=CH—CH=CH— (a-3);

wherein each hydrogen atom in the radicals (a-1) to (a-3) may independently be replaced by $R^6$ wherein $R^6$ is selected from $C_{1-6}$alkyl, halo, hydroxy, $C_{1-6}$alkyloxy, ethenyl substituted with carboxyl or $C_{1-6}$alkyloxycarbonyl, hydroxy$C_{1-6}$alkyl, formyl, carboxyl or hydroxycarbonyl$C_{1-6}$alkyl;

each Y independently is a bivalent radical of formula —O—, —S— or —NR^7—;

wherein $R^7$ is hydrogen, $C_{1-6}$alkyl or $C_{1-6}$alkylcarbonyl;

Z is a bivalent radical of formula

—(CH_2)_p— (b-1),

—CH=CH— (b-2),

—CH_2—CHOH— (b-3),

—CH_2—O— (b-4),

—CH_2—C(=O)— (b-5), or

—CH_2—C(=NOH)— (b-6), with the proviso that the bivalent radicals (b-3), (b-4), (b-5) and (b-6) are connected to the nitrogen of the imidazole ring via their —CH_2-moiety;

wherein p is 1, 2, 3 or 4;

L is hydrogen; $C_{1-6}$alkyl; $C_{2-6}$alkenyl; $C_{1-6}$alkylcarbonyl; $C_{1-6}$alkyloxycarbonyl; $C_{1-6}$alkyl substituted with one or more substituents each independently selected from hydroxy, carboxyl, $C_{1-6}$alkyloxy, $C_{1-6}$alkyloxycarbonyl, aryl, aryloxy, cyano or $R^8$HN— wherein $R^8$ is hydrogen, $C_{1-6}$alkyl, $C_{1-6}$alkyloxycarbonyl, or $C_{1-6}$alkylcarbonyl; or L represents a radical of formula -Alk-Y^1—Het^1 (I-1), -Alk-NH—CO—Het^2 (c-2) or -Alk-Het^3 (c-3); wherein Alk represents $C_{1-4}$alkanediyl;

$Y^1$ represents O, S or NH;

Het^1 and Het^2 each represent furanyl, tetrahydrofuranyl, thienyl, oxazolyl, thiazolyl or imidazolyl each optionally substituted with one or two $C_{1-4}$alkyl substituents; pyrrolyl or pyrazolyl optionally substituted with formyl, hydroxy$C_{1-4}$alkyl, hydroxycarbonyl, $C_{1-4}$alkyloxycarbonyl or with one or two $C_{1-4}$alkyl substituents; thiadiazolyl or oxadiazolyl optionally substituted with amino or $C_{1-4}$alkyl; pyridinyl, pyrimidinyl, pyrazinyl or pyridazinyl each optionally substituted with $C_{1-4}$alkyl, $C_{1-4}$alkyloxy, amino, hydroxy or halo; and Het^3 represents furanyl, tetrahydrofuranyl, thienyl, oxazolyl, thiazolyl or imidazolyl each optionally substituted with one or two $C_{1-4}$alkyl substituents; pyrrolyl or pyrazolyl optionally substituted with formyl, hydroxy$C_{1-4}$alkyl, hydroxycarbonyl, $C_{1-4}$alkyloxycarbonyl or with one or two $C_{1-4}$alkyl substituents; thiadiazolyl or oxadiazolyl optionally substituted with amino or $C_{1-4}$alkyl; pyridinyl, pyrimidinyl, pyrazinyl or pyridazinyl each optionally substituted with $C_{1-4}$alkyl, $C_{1-4}$alkyloxy, amino, hydroxy, halo, 4,5-dihydro-5-oxo-1H-tetrazolyl substituted with $C_{1-4}$alkyl, 2-oxo-3-oxazolidinyl, 2,3-dihydro-2-oxo-1H-benzimidazol-1-yl or a radical of formula

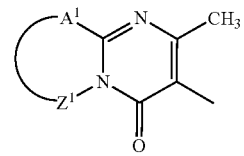

wherein $A^1$—$Z^1$ represents S—CH=CH, S—CH_2—CH_2, S—CH_2—CH_2—CH_2, CH=CH—CH=CH, or CH_2—CH_2—CH_2—CH_2;

aryl is phenyl or phenyl substituted with 1, 2 or 3 substituents each independently selected from halo, hydroxy, $C_{1-4}$alkyl, polyhalo$C_{1-4}$alkyl, cyano, aminocarbonyl, $C_{1-4}$alkyloxy or polyhalo$C_{1-4}$alkyloxy;

with the proviso that 5,6-dihydrospiro[imidazo[2,1-b][3]benzazepine-11[11H],4'-piperidine] and pharmaceutically acceptable addition salts thereof are not included, and 6,11-dihydro-1'-(phenylmethyl)-5H-spiro[imidazo[2,1-b][3]benzazepine-11,4'-piperidine] (E)-2-butenedioate (1:2) is not included.

2. A compound according to claim 1 wherein L is hydrogen, $C_{1-6}$alkyl, $C_{1-6}$alkylcarbonyl, $C_{1-6}$alkyloxycarbonyl or $C_{1-6}$alkyl substituted with hydroxy, carboxyl, $C_{1-6}$alkyloxy or $C_{1-6}$alkyloxycarbonyl.

3. A compound according to claim 1 wherein L is $C_{1-6}$alkyl substituted with aryl and $C_{1-6}$alkyloxycarbonyl.

4. A compound according to claim 1 wherein —A—B— is a bivalent radical of formula —CH=CH—CH=CH— (a-3) or —CH=CH—Y— (a-2).

5. A compound according to claim 1 wherein Z is —$(CH_2)_p$— (b-1), —CH=CH— (b-2), or —$CH_2$—O— (b-4).

6. A compound according to claim 1, wherein L is hydrogen, $C_{1-6}$alkyl, hydroxy$C_{1-6}$alkyl, carboxy$C_{1-6}$alkyl, $C_{1-6}$alkyloxycarbonyl, or $C_{1-6}$alkyloxycarbonyl$C_{1-6}$alkyl.

7. A compound according to claim 1 wherein $R^1$ is hydroxy$C_{1-6}$alkyl, formyl, $C_{1-6}$alkyloxycarbonyl, $C_{1-6}$alkyloxy$C_{1-6}$alkyl, $N(R^3R^4)C(=O)$—, halo or hydrogen.

8. A compound according to claim 1 wherein the compound is 5,6-dihydrospiro[11H-imidazo[2,1-b][3]benzazepine-11,4'-piperidine]-3-carboxamide dihydrochloride;

1'-butyl-5,6-dihydrospiro[imidazo[2,1-b][3]benzazepine-11-[11H],4'-piperidine];

6,11-dihydro-1'-methylspiro[5H-imidazo[2,1-b][3]benzazepine-11,4'-piperidine]cyclohexylsulfamate (1:2);

6,11-dihydrospiro[5-imidazo[2,1-b][3]benzazepine-11,4'-piperidine]-3-methanol (E)-2-butenedioate (2:1);

3-chloro-6,11-dihydrospiro[5H-imidazo[2,1-b][3]benzazepine-11,4'-piperidine] (E)-2-butenedioate (1:1);

6,11-dihydro-3-(methoxymethyl)spiro[5H-imidazo[2,1-b][3]benzazepine-11,4'-piperidine] (E)-2-butenedioate (1:1);

6,11-dihydro-1'-(2-hydroxyethyl)spiro[5H-imidazo[2,1-b][3]benzazepine-11,4'-piperidine]-3-carboxamide;

6,11-dihydro-1'-methylspiro[5H-imidazo[2,1-b][3]benzazepine-11,4'-piperidine]-3-carboxamide monohydrate;

ethyl 3-(aminocarbonyl)-6,11-dihydro-α-phenylspiro[5H-imidazo[2,1-b][3]-benzazepine-11,4'-piperidine]-1'-propanoate monohydrochloride;

3-(aminocarbonyl)-6,11-dihydrospiro[5H-imidazo[2,1-b][3]-benzazepine-11,4'-piperidine]-1'-carboxylate;

spiro[10H-imidazo[1,2-a]thieno[3,2-d]azepine-10,4'-piperidine];

6,11-dihydrospiro[5H-imidazo[2,1-b][3]benzazepine-11,4'-piperidine]-2,3-dicarboxamide dihydrochloride monohydrate; or a N-oxide, an addition salt, a quaternary amine or a stereochemically isomeric form thereof.

9. A pharmaceutical composition comprising a pharmaceutically acceptable carrier, and as active ingredient a therapeutically effective amount of a compound as defined in claim 1.

10. A process of preparing a pharmaceutical composition, comprising mixing a pharmaceutically acceptable carrier with a therapeutically effective amount of a compound as defined in claim 1.

11. A compound of formula

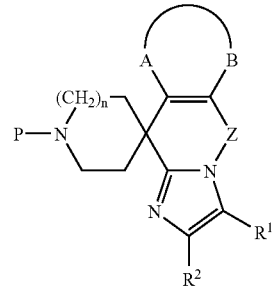

(II-a)

or a N-oxide, an addition salt, a quaternary amine or a stereochemically isomeric form thereof wherein P is a protective group and n, —A—B—, Z, $R^1$ and $R^2$ are defined as in claim 1, with the proviso that 6,11-dihydro-1'-(phenylmethyl)-5H-spiro[imidazo[2,1-b][3]-benzazepine-11,4'-piperidine] (E)-2-butenedioate (1:2) is not included.

12. A compound according to claim 11 wherein P is benzyl.

13. A process of preparing a compound as claimed in claim 1, comprising a) deprotecting an intermediate of formula (II), followed optionally by derivatizing either the piperidine moiety, or the imidazole moiety, or both the piperidine moiety and the imidazole moiety

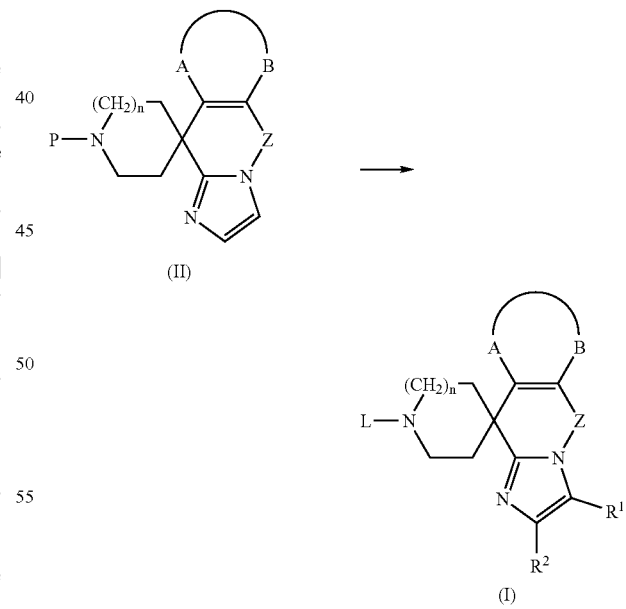

with P being a protective group;

b) derivatizing an intermediate of formula (II) at the imidazole moiety, to form an intermediate of formula (II-a), followed by deprotecting the piperidine moiety, and followed optionally by derivatizing the piperidine moiety

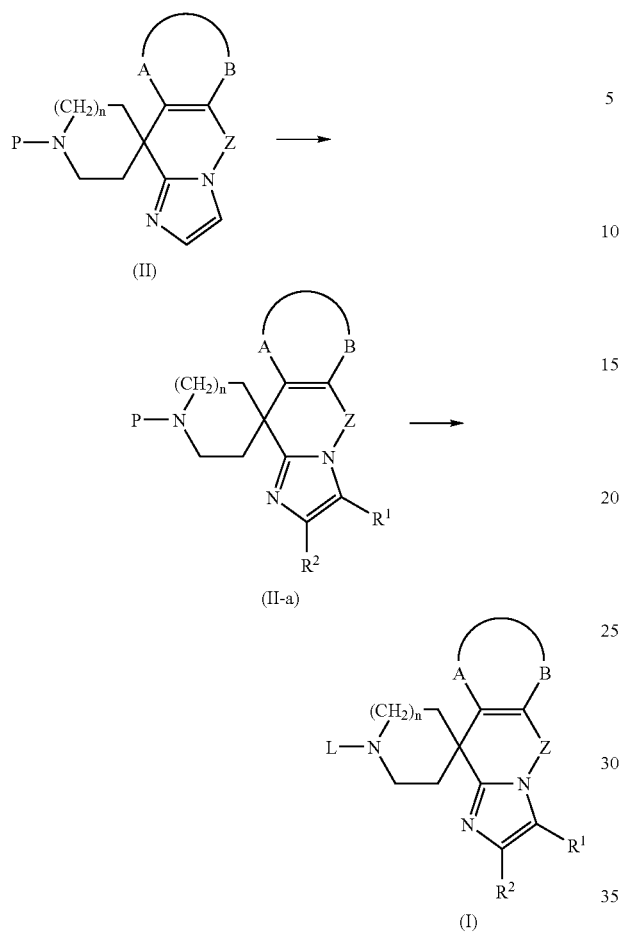

c) cyclizing an intermediate of formula (III) in the presence of an appropriate acid, to form a compound of formula (I-a)

and, optionally, converting compounds of formula (I) and (I-a) into each other, and further, optionally, converting the compounds of formula (I), into a therapeutically active non-toxic acid addition salt by treatment with an acid, or into a therapeutically active non-toxic base addition salt by treatment with a base, or converting the acid addition salt form into the free base by treatment with alkali, or converting the base addition salt into the free acid by treatment with acid; and, optionally, preparing stereochemically isomeric forms or N-oxide forms thereof.

14. A process of preparing a compound as claimed in claim 12, comprising, a) cyclizing a compound of formula (XI) with an appropriate acid, to form a compound of formula (II-k), followed optionally by derivatizing the imidazole moiety, to form a compound of formula (II-a-1)

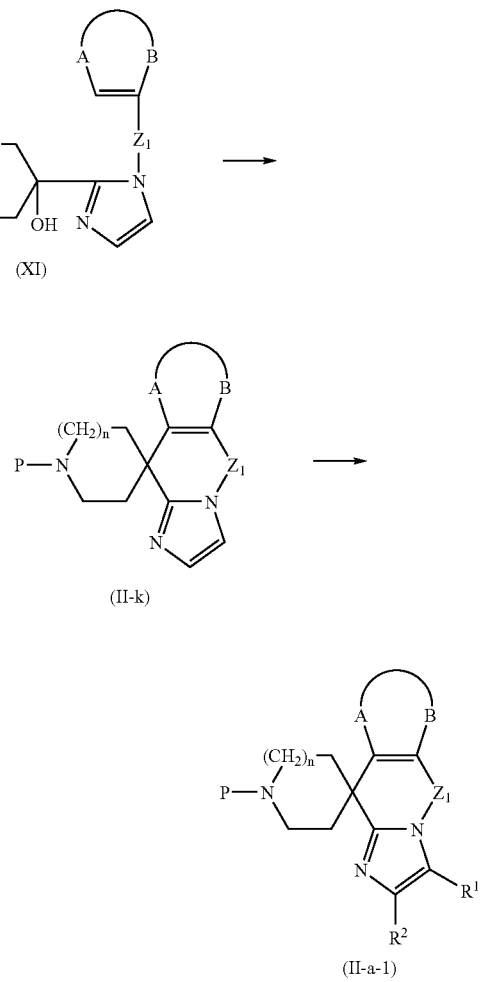

with $Z_1$ being a bivalent radical of formula $-(CH_2)_p-$, wherein p is 1,2,3 or 4; and b) reacting a tricyclic moiety of formula (XIV) with a reagent of formula (XV) under an inert atmosphere in a reaction inert solvent in the presence of a suitable base, to form a compound of formula (II-1), followed optionally by derivatizing the imidazole moiety to form a compound of formula (II-a-2)

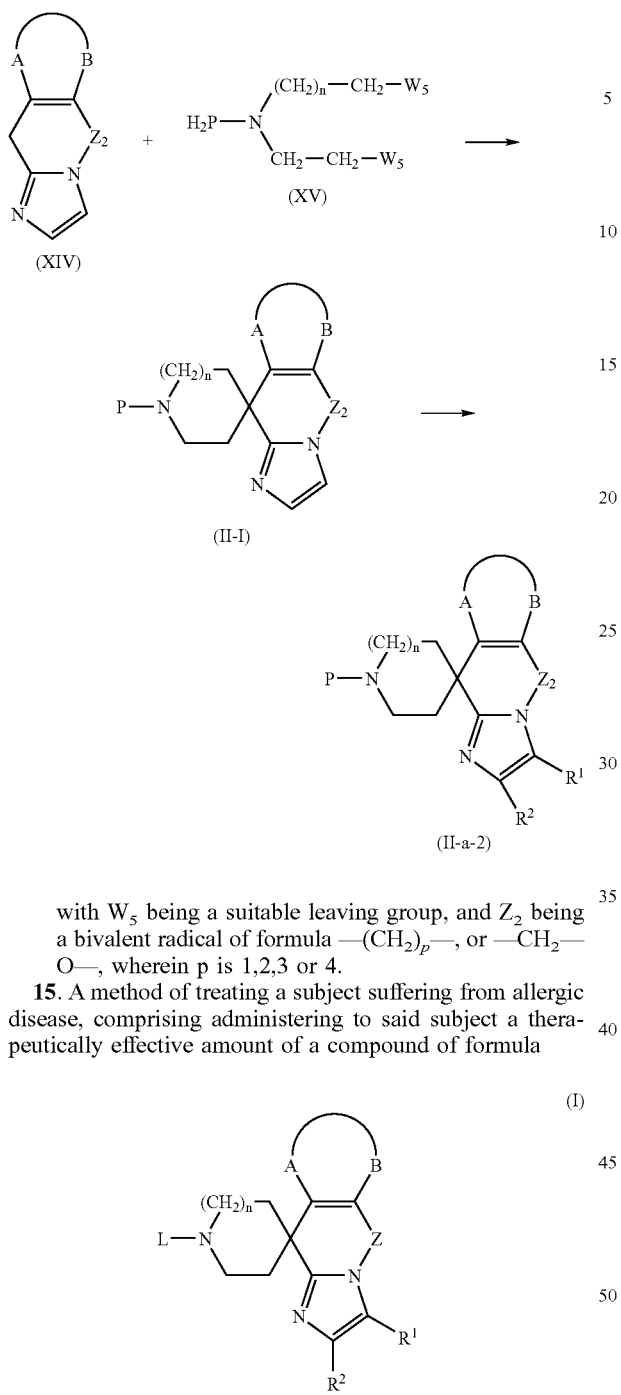

with $W_5$ being a suitable leaving group, and $Z_2$ being a bivalent radical of formula $—(CH_2)_p—$, or $—CH_2—O—$, wherein p is 1,2,3 or 4.

15. A method of treating a subject suffering from allergic disease, comprising administering to said subject a therapeutically effective amount of a compound of formula (I)

or a N-oxide, an addition salt, a quaternary amine or a stereochemically isomeric form thereof wherein $R^1$ is hydrogen, $C_{1-6}$alkyl, halo, formyl, carboxyl, $C_{1-6}$alkyloxycarbonyl, $C_{1-6}$alkylcarbonyl, $N(R^3R^4)C(=O)—$, $N(R^3R^4)C(=O)N(R^5)—$, ethenyl substituted with carboxyl or $C_{1-6}$alkyloxycarbonyl, or $C_{1-6}$alkyl substituted with hydroxy, carboxyl, $C_{1-6}$alkyloxy, $C_{1-6}$alkyloxycarbonyl, $N(R^3R^4)C(=O)—$, $C_{1-6}$alkylC(=O)N(R^5)—$, $C_{1-6}$alkylS(=O)_2N(R^5)—$ or $N(R^3R^4)C(=O)N(R^5)—$;

wherein each $R^3$ and each $R^4$ independently are hydrogen or $C_{1-4}$alkyl;

$R^5$ is hydrogen or hydroxy;

$R^2$ is hydrogen, $C_{1-6}$alkyl, hydroxy$C_{1-6}$alkyl, $C_{1-6}$alkyloxy$C_{1-6}$alkyl, $N(R^3R^4)C(=O)—$, aryl or halo;

n is 1 or 2;

—A—B— represents a bivalent radical of formula $—Y—CH=CH—$ (a-1);

$—CH=CH—Y—$ (a-2); or $—CH=CH—CH=CH—$ (a-3);

wherein each hydrogen atom in the radicals (a-1) to (a-3) may independently be replaced by $R^6$ wherein $R^6$ is selected from $C_{1-6}$alkyl, halo, hydroxy, $C_{1-6}$alkyloxy, ethenyl substituted with carboxyl or $C_{1-6}$alkyloxycarbonyl, hydroxy$C_{1-6}$alkyl, formyl, carboxyl or hydroxycarbonyl$C_{1-6}$alkyl;

each Y independently is a bivalent radical of formula $—O—$, $—S—$ or $—NR^7—$;

wherein $R^7$ is hydrogen, $C_{1-6}$alkyl or $C_{1-6}$alkylcarbonyl;

Z is a bivalent radical of formula $—(CH_2)_p—$ (b-1), $—CH=CH—$ (b-2), $—CH_2—CHOH—$ (b-3), $—CH_2—O—$ (b-4), $—CH_2—C(=O)—$ (b-5), or $—CH_2—C(=NOH)—$ (b-6), with the proviso that the bivalent radicals (b-3), (b-4), (b-5) and (b-6) are connected to the nitrogen of the imidazole ring via their $—CH_2$-moiety;

wherein p is 1, 2, 3 or 4;

L is hydrogen; $C_{1-6}$alkyl; $C_{2-6}$alkenyl; $C_{1-6}$alkylcarbonyl; $C_{1-6}$alkyloxycarbonyl; $C_{1-6}$alkyl substituted with one or more substituents each independently selected from hydroxy, carboxyl, $C_{1-6}$alkyloxy, $C_{1-6}$alkyloxycarbonyl, aryl, aryloxy, cyano or $R^8$HN— wherein $R^8$ is hydrogen, $C_{1-6}$alkyl, $C_{1-6}$alkyloxycarbonyl, or $C_{1-6}$alkylcarbonyl; or L represents a radical of formula -Alk-$Y^1$—Het$^1$ (I-1), -Alk-NH—CO—Het$^2$ (c-2) or -Alk-Het$^3$ (c-3); wherein Alk represents $C_{1-4}$alkanediyl;

$Y^1$ represents O, S or NH;

Het$^1$ and Het$^2$ each represent furanyl, tetrahydrofuranyl, thienyl, oxazolyl, thiazolyl or imidazolyl each optionally substituted with one or two $C_{1-4}$alkyl substituents; pyrrolyl or pyrazolyl optionally substituted with formyl, hydroxy$C_{1-4}$alkyl, hydroxycarbonyl, $C_{1-4}$alkyloxycarbonyl or with one or two $C_{1-4}$alkyl substituents; thiadiazolyl or oxadiazolyl optionally substituted with amino or $C_{1-4}$alkyl; pyridinyl, pyrimidinyl, pyrazinyl or pyridazinyl each optionally substituted with $C_{1-4}$alkyl, $C_{1-4}$alkyloxy, amino, hydroxy or halo; and Het³ represents furanyl, tetrahydrofuranyl, thienyl, oxazolyl, thiazolyl or imidazolyl each optionally substituted with one or two $C_{1-4}$alkyl substituents; pyrrolyl or pyrazolyl optionally substituted with formyl, hydroxy$C_{1-4}$alkyl, hydroxycarbonyl, $C_{1-4}$alkyloxycarbonyl or with one or two $C_{1-4}$alkyl substituents; thiadiazolyl or oxadiazolyl optionally substituted with amino or $C_{1-4}$alkyl; pyridinyl, pyrimidinyl, pyrazinyl or pyridazinyl each optionally substituted with $C_{1-4}$alkyl, $C_{1-4}$alkyloxy, amino, hydroxy, halo, 4,5-dihydro-5-oxo-1H-tetrazolyl substituted with $C_{1-4}$alkyl, 2-oxo-3-oxazolidinyl, 2,3-dihydro-2-oxo-1H-benzimidazol-1-yl or a radical of formula

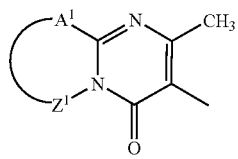

wherein $A^1$—$Z^1$ represents S—CH=CH, S—CH₂—CH₂, S—CH₂—CH₂—CH₂, CH=CH—CH=CH, or CH₂—CH₂—CH₂—CH₂;

aryl is phenyl or phenyl substituted with 1, 2 or 3 substituents each independently selected from halo, hydroxy, $C_{1-4}$alkyl, polyhalo$C_{1-4}$alkyl, cyano, aminocarbonyl, $C_{1-4}$alkyloxy or polyhalo$C_{1-4}$alkyloxy;

with the proviso that 5,6-dihydrospiro[imidazo[2,1-b][3]benzazepine-11[11H],4'-piperidine] and pharmaceutically acceptable addition salts thereof are not included, and 6,11-dihydro-1'-(phenylmethyl)-5H-spiro[imidazo[2,1-b][3]benzazepine-11,4'-piperidine] (E)-2-butenedioate (1:2) is not included.

\* \* \* \* \*

UNITED STATES PATENT AND TRADEMARK OFFICE
CERTIFICATE OF CORRECTION

| | | |
|---|---|---|
| PATENT NO. | : 7,148,214 B1 | |
| APPLICATION NO. | : 09/868535 | |
| DATED | : December 12, 2006 | |
| INVENTOR(S) | : Frans Eduard Janssens et al. | |

It is certified that error appears in the above-identified patent and that said Letters Patent is hereby corrected as shown below:

Column 1,
Line 8, delete "antihistarminic" and insert -- antihistaminic --.
Line 19, delete "antihistarminic" and insert -- antihistaminic --.

Column 4,
Line 37, delete "(a)" and insert -- (I) --.

Column 33,
Line 49, delete "(86" and insert -- (86%) (comp. 6a; not claimed). A fraction obtained in said way, --.

Column 35,
Line 21, delete "[11H-midazo" and insert -- [11H-imidazo --.

Column 38,
Line 8, delete "Was" and insert -- was --.

Column 41,
Line 7, delete "9812," and insert -- 98/2, --.

Column 43,
Line 9, delete "dihydrospiro" and insert -- dihydro-spiro --.

Column 52,
Line 19, delete "(I-1)," and insert -- (c-1), --.

Column 53,
Line 3, delete "are not included".
Line 5, delete "(E)-2-butenedioate (1:2) is" and insert -- and pharmaceutically acceptable addition salts thereof are --.

Column 54,
Line 25, delete "(E)-2-butenedioate (1 :2) is" and insert -- and pharmaceutically acceptable addition salts thereof are --.

UNITED STATES PATENT AND TRADEMARK OFFICE
CERTIFICATE OF CORRECTION

| | |
|---|---|
| PATENT NO. | : 7,148,214 B1 |
| APPLICATION NO. | : 09/868535 |
| DATED | : December 12, 2006 |
| INVENTOR(S) | : Frans Eduard Janssens et al. |

It is certified that error appears in the above-identified patent and that said Letters Patent is hereby corrected as shown below:

Column 58,
Line 49, delete "(I-1)," and insert -- (c-1), --.

Signed and Sealed this

Eleventh Day of December, 2007

JON W. DUDAS
*Director of the United States Patent and Trademark Office*